US 12,329,122 B2

(12) United States Patent
Stuessel et al.

(10) Patent No.: US 12,329,122 B2
(45) Date of Patent: Jun. 17, 2025

(54) AUTOMATED TEAT DIP FLUID MANIFOLD

(71) Applicant: GEA FARM TECHNOLOGIES GMBH, Bönen (DE)

(72) Inventors: Matthew J. Stuessel, Alma Center, WI (US); Wolfgang Schulze-Wilmert, Gronau (DE); Thomas Orban, Dortmund (DE)

(73) Assignee: GEA Farm Technologies GmbH, Bönen (DE)

( * ) Notice: Subject to any disclaimer, the term of this patent is extended or adjusted under 35 U.S.C. 154(b) by 176 days.

(21) Appl. No.: 18/115,848

(22) Filed: Mar. 1, 2023

(65) Prior Publication Data

US 2023/0200345 A1    Jun. 29, 2023

Related U.S. Application Data

(63) Continuation of application No. 16/178,996, filed on Nov. 2, 2018, now Pat. No. 11,617,343.

(60) Provisional application No. 62/581,514, filed on Nov. 3, 2017, provisional application No. 62/581,526, filed on Nov. 3, 2017.

(51) Int. Cl.
| | |
|---|---|
| *A01J 7/04* | (2006.01) |
| *A01J 5/007* | (2006.01) |
| *A01J 5/04* | (2006.01) |
| *A01J 7/02* | (2006.01) |
| *A61K 9/00* | (2006.01) |
| *F16L 55/07* | (2006.01) |

(52) U.S. Cl.
CPC .................. *A01J 7/04* (2013.01); *A01J 5/007* (2013.01); *A01J 5/044* (2013.01); *A01J 7/022* (2013.01); *A61K 9/0041* (2013.01); *F16L 55/07* (2013.01); *F16L 2201/20* (2013.01); *F16L 2201/30* (2013.01)

(58) Field of Classification Search
CPC ...... A01J 5/00; A01J 5/007; A01J 5/01; A01J 5/025; A01J 5/04; A01J 5/044; A01J 7/00; A01J 7/005; A01J 7/02; A01J 7/022; A01J 7/025; A01J 7/027; A01J 7/04
USPC ................................ 119/14.08, 14.18, 14.47
See application file for complete search history.

(56) References Cited

U.S. PATENT DOCUMENTS

| | | | |
|---|---|---|---|
| 1,365,665 | A | 1/1921 | Davies |
| 2,012,031 | A | 8/1935 | Woodruff |
| 2,532,088 | A | 11/1950 | Cordis |
| 2,747,544 | A | 5/1956 | Thomas |
| 3,014,455 | A | 12/1961 | Olander |

(Continued)

FOREIGN PATENT DOCUMENTS

| | | |
|---|---|---|
| AU | 641229 B2 | 9/1993 |
| AU | 2013294747 B2 | 11/2016 |

(Continued)

OTHER PUBLICATIONS

Merged translation of DE 10006548 A1 (Year: 2001).*

(Continued)

*Primary Examiner* — Peter M Poon
*Assistant Examiner* — Danielle A Clerkley
(74) *Attorney, Agent, or Firm* — PATENT PORTFOLIO BUILDERS PLLC

(57) ABSTRACT

A teat dip fluid manifold and methods for distributing teat dip fluids, and including redundant valve sets and pressure monitoring between valve pairs to determine valve condition.

7 Claims, 17 Drawing Sheets

(56) References Cited

U.S. PATENT DOCUMENTS

| | | |
|---|---|---|
| 3,099,246 A | 7/1963 | Beskow |
| 3,119,401 A | 1/1964 | Merritt et al. |
| 3,285,297 A | 11/1966 | Duft et al. |
| 3,417,763 A | 12/1968 | Fjermestad et al. |
| 3,461,845 A | 8/1969 | Peterson |
| 3,474,760 A | 10/1969 | Siddall et al. |
| 3,482,547 A | 12/1969 | Jakob |
| 3,500,839 A | 3/1970 | Bender |
| 3,630,081 A | 12/1971 | Nelson |
| 3,648,696 A | 3/1972 | Keith |
| 3,688,783 A | 9/1972 | Owens |
| 3,696,790 A | 10/1972 | Albright |
| 3,713,423 A | 1/1973 | Sparr |
| 3,726,253 A | 4/1973 | Duncan |
| 3,762,371 A | 10/1973 | Quayle et al. |
| 3,789,798 A | 2/1974 | Reisgies et al. |
| 3,797,525 A | 3/1974 | Lieser |
| 3,861,335 A | 1/1975 | Przewalski |
| 3,861,355 A | 1/1975 | Johnson et al. |
| 3,957,018 A | 5/1976 | Barrett |
| 3,971,512 A | 7/1976 | Duncan |
| 3,973,520 A | 8/1976 | Flocchini |
| 3,989,009 A | 11/1976 | Robar et al. |
| 4,034,714 A | 7/1977 | Umbaugh et al. |
| 4,061,504 A | 12/1977 | Zall et al. |
| 4,149,489 A | 4/1979 | Umbaugh et al. |
| 4,168,677 A | 9/1979 | Brown |
| 4,175,514 A | 11/1979 | Souza et al. |
| 4,177,760 A | 12/1979 | Slater |
| 4,222,346 A | 9/1980 | Reisgies |
| 4,253,421 A | 3/1981 | Slater et al. |
| 4,254,754 A | 3/1981 | Takada et al. |
| 4,295,490 A | 10/1981 | Boudreau |
| 4,305,346 A | 12/1981 | Sparr, Sr. |
| 4,332,215 A | 6/1982 | Larson |
| 4,333,387 A | 6/1982 | Seitz |
| 4,333,421 A | 6/1982 | Schluckbier |
| 4,344,385 A | 8/1982 | Swanson et al. |
| 4,372,345 A | 2/1983 | Mehus |
| 4,378,757 A | 4/1983 | Hamann |
| 4,393,811 A | 7/1983 | Bodmin |
| 4,395,971 A | 8/1983 | Happel et al. |
| 4,403,568 A | 9/1983 | Fukuhara et al. |
| 4,403,569 A | 9/1983 | Bennett |
| 4,459,938 A | 7/1984 | Noorlander |
| 4,462,425 A | 7/1984 | Mehus |
| 4,485,762 A | 12/1984 | Sutton et al. |
| 4,498,419 A | 2/1985 | Flocchini |
| 4,516,530 A | 5/1985 | Reisgies et al. |
| 4,572,105 A | 2/1986 | Chowdhury et al. |
| 4,586,462 A | 5/1986 | Icking |
| 4,593,649 A | 6/1986 | Britten |
| 4,903,639 A | 2/1990 | Kessel |
| 4,907,535 A | 3/1990 | Matsuzawa et al. |
| 4,924,809 A | 5/1990 | Verbrugge |
| 4,936,254 A | 6/1990 | Marshall |
| 5,052,341 A | 10/1991 | Woolford et al. |
| 5,101,770 A | 4/1992 | Stevenson |
| 5,134,967 A | 8/1992 | Marshall |
| 5,161,482 A | 11/1992 | Griffin |
| 5,166,313 A | 11/1992 | Archibald et al. |
| 5,167,201 A | 12/1992 | Peles |
| 5,178,095 A | 1/1993 | Mein |
| 5,218,924 A | 6/1993 | Thompson et al. |
| 5,255,628 A | 10/1993 | Kristoffer |
| 5,379,722 A | 1/1995 | Larson |
| 5,386,799 A | 2/1995 | Dietrich |
| 5,390,627 A | 2/1995 | van der Berg et al. |
| 5,403,005 A | 4/1995 | Avila-Valdez |
| 5,493,995 A | 2/1996 | Chowdhury |
| 5,568,788 A | 10/1996 | van den Berg et al. |
| 5,572,947 A | 11/1996 | Larson et al. |
| 5,673,650 A | 10/1997 | Mottram et al. |
| 5,697,325 A | 12/1997 | Gehm et al. |
| 5,722,343 A | 3/1998 | Aurik et al. |
| 5,769,025 A | 6/1998 | van der Lely et al. |
| 5,778,820 A | 7/1998 | van der Lely et al. |
| 5,850,845 A | 12/1998 | Pereira et al. |
| 5,881,669 A | 3/1999 | van den Berg et al. |
| 5,896,828 A | 4/1999 | Kronschnabel et al. |
| 5,909,716 A | 6/1999 | van der Lely |
| 5,934,220 A | 8/1999 | Hall et al. |
| 5,957,081 A | 9/1999 | van der Lely et al. |
| 5,960,736 A | 10/1999 | Ludington et al. |
| 5,992,347 A | 11/1999 | Innings et al. |
| 6,009,833 A | 1/2000 | van der Lely |
| 6,079,359 A | 6/2000 | van den Berg |
| 6,089,242 A | 7/2000 | Buck |
| 6,098,570 A | 8/2000 | Aurik et al. |
| 6,202,593 B1 | 3/2001 | Maier et al. |
| 6,234,110 B1 | 5/2001 | Xavier |
| 6,244,215 B1 | 6/2001 | Oosterling |
| 6,267,077 B1 | 7/2001 | van den Berg et al. |
| 6,276,297 B1 | 8/2001 | van den Berg et al. |
| 6,308,655 B1 | 10/2001 | Oosterling |
| 6,318,299 B1 | 11/2001 | Birk |
| 6,321,682 B1 | 11/2001 | Eriksson et al. |
| 6,367,416 B1 | 4/2002 | van der Lely et al. |
| 6,371,046 B1 | 4/2002 | Petterson et al. |
| 6,435,132 B1 | 8/2002 | Milbrath et al. |
| 6,546,893 B1 | 4/2003 | Happel et al. |
| 6,550,420 B1 | 4/2003 | Bjork |
| 6,561,126 B2 | 5/2003 | Forsen et al. |
| 6,584,930 B2 | 7/2003 | Buecker |
| 6,591,784 B1 | 7/2003 | Eriksson |
| 6,598,560 B1 | 7/2003 | van den Berg |
| 6,619,227 B1 | 9/2003 | Berger et al. |
| 6,626,130 B1 | 9/2003 | Eriksson |
| 6,644,240 B1 | 11/2003 | Dietrich |
| 6,752,102 B2 | 6/2004 | Dalh et al. |
| 6,755,153 B1 | 6/2004 | Chowdhury |
| 6,935,270 B2 | 8/2005 | Wipperfurth et al. |
| 6,997,135 B1 | 2/2006 | Dewaard |
| 6,997,136 B1 | 2/2006 | Coates |
| 7,036,981 B2 | 5/2006 | Veenstra et al. |
| 7,128,020 B2 | 10/2006 | Bjork et al. |
| 7,143,718 B2 | 12/2006 | Bosma et al. |
| 7,162,970 B2 | 1/2007 | Maier et al. |
| 7,174,848 B2 | 2/2007 | Brown et al. |
| 7,178,480 B2 | 2/2007 | Dahl et al. |
| 7,237,694 B2 | 7/2007 | Freudinger |
| 7,263,948 B2 | 9/2007 | Ericsson et al. |
| 7,281,493 B2 | 10/2007 | Dietrich |
| 7,290,497 B2 | 11/2007 | Rottier et al. |
| 7,299,766 B2 | 11/2007 | Van den Berg et al. |
| 7,350,478 B2 | 4/2008 | Fernandez |
| 7,377,232 B2 | 5/2008 | Holmgren et al. |
| 7,401,573 B2 | 7/2008 | Torgerson |
| 7,412,943 B2 | 8/2008 | Ericsson et al. |
| 7,484,474 B2 | 2/2009 | Van Den Berg et al. |
| 7,536,975 B2 | 5/2009 | Denes et al. |
| 7,575,022 B2 | 8/2009 | Higgins |
| 7,578,260 B2 | 8/2009 | Shin |
| 7,707,966 B2 | 5/2010 | Torgerson et al. |
| 7,765,951 B2 | 8/2010 | Dietrich |
| 7,793,614 B2 | 9/2010 | Ericsson et al. |
| 7,926,449 B2 | 4/2011 | Stellnert et al. |
| 7,963,249 B2 | 6/2011 | Duke |
| 8,025,029 B2 | 9/2011 | Torgerson et al. |
| 8,033,247 B2 | 10/2011 | Torgerson et al. |
| 8,117,989 B2 | 2/2012 | Torgerson et al. |
| 8,191,507 B2 | 6/2012 | Persson et al. |
| 8,210,123 B2 | 7/2012 | Duke |
| 8,240,272 B2 | 8/2012 | Duke |
| 8,286,653 B2 | 10/2012 | Lidman et al. |
| 8,342,125 B2 | 1/2013 | Torgerson et al. |
| 8,590,486 B2 | 11/2013 | Torgerson et al. |
| 8,677,937 B2 | 3/2014 | Shin |
| 8,770,146 B2 | 7/2014 | Buck et al. |
| 8,925,483 B2 | 1/2015 | Torgerson et al. |
| 8,991,335 B2 | 3/2015 | Torgerson et al. |
| 9,016,238 B2 | 4/2015 | Duke |
| 9,049,835 B2 | 6/2015 | Duke |
| 9,072,272 B2 | 7/2015 | Bosma et al. |

(56) References Cited

U.S. PATENT DOCUMENTS

| | | |
|---|---|---|
| 9,072,273 B2 | 7/2015 | Torgerson et al. |
| 9,332,726 B2 | 5/2016 | Bosma et al. |
| 9,468,189 B2 | 10/2016 | Torgerson et al. |
| 9,468,190 B2 | 10/2016 | Duke et al. |
| 9,510,556 B2 | 12/2016 | Torgerson et al. |
| 9,526,224 B2 | 12/2016 | Balkenhol et al. |
| 9,545,079 B2 | 1/2017 | Torgerson et al. |
| 9,686,958 B2 | 6/2017 | Sellner et al. |
| 9,763,421 B2 | 9/2017 | Torgerson et al. |
| 9,770,006 B2 | 9/2017 | Torgerson et al. |
| 9,883,652 B2 | 2/2018 | Torgerson et al. |
| 9,930,862 B2 | 4/2018 | Hofman et al. |
| 10,123,506 B2 | 11/2018 | Bosma |
| 10,426,128 B2 | 10/2019 | Balkenhol et al. |
| 10,499,610 B2 | 12/2019 | Torgerson et al. |
| 10,502,330 B2 | 12/2019 | Balkenhol |
| 10,514,316 B2 | 12/2019 | Enickl |
| 10,681,895 B2 | 6/2020 | Sellner et al. |
| 2002/0185071 A1 | 12/2002 | Guo |
| 2004/0089242 A1 | 5/2004 | Verstege et al. |
| 2004/0231603 A1 | 11/2004 | Bjork et al. |
| 2005/0274327 A1 | 12/2005 | Johnsson et al. |
| 2006/0016399 A1 | 1/2006 | Torgerson |
| 2006/0037542 A1 | 2/2006 | Denes et al. |
| 2006/0112887 A1 | 6/2006 | Brown et al. |
| 2007/0070803 A1 | 3/2007 | Urquhart |
| 2007/0157887 A1 | 7/2007 | Fernandez |
| 2007/0186860 A1 | 8/2007 | Theodorus Dietrich |
| 2007/0215053 A1 | 9/2007 | Duke |
| 2007/0277737 A1 | 12/2007 | Maier et al. |
| 2008/0022932 A1 | 1/2008 | Rottier et al. |
| 2008/0202433 A1 | 8/2008 | Duke |
| 2008/0276871 A1 | 11/2008 | Auburger et al. |
| 2008/0314322 A1 | 12/2008 | Stellnert et al. |
| 2009/0050061 A1 | 2/2009 | Duke |
| 2009/0050062 A1 | 2/2009 | Auburger et al. |
| 2009/0064937 A1 | 3/2009 | Rottier et al. |
| 2009/0151641 A1 | 6/2009 | Schulze Wartenhorst et al. |
| 2009/0165724 A1 | 7/2009 | Mader et al. |
| 2009/0320760 A1 | 12/2009 | Torgerson et al. |
| 2010/0132626 A1 | 6/2010 | Torgerson et al. |
| 2010/0154900 A1 | 6/2010 | Torgerson et al. |
| 2010/0236487 A1 | 9/2010 | Stellnert et al. |
| 2010/0326360 A1 | 12/2010 | Duke et al. |
| 2011/0220028 A1 | 9/2011 | Duke |
| 2011/0220160 A1 | 9/2011 | Bosma |
| 2011/0232575 A1 | 9/2011 | Duke |
| 2012/0111275 A1 | 5/2012 | Torgerson et al. |
| 2012/0118237 A1 | 5/2012 | Torgerson et al. |
| 2012/0118238 A1 | 5/2012 | Torgerson et al. |
| 2012/0272911 A1 | 11/2012 | Duke |
| 2013/0199449 A1 | 8/2013 | Daniel |
| 2014/0283751 A1 | 9/2014 | Buck et al. |
| 2015/0173320 A1 | 6/2015 | Balkenhol et al. |
| 2015/0201577 A1 | 7/2015 | Duke |
| 2015/0260302 A1 | 9/2015 | Peterson et al. |
| 2015/0296736 A1* | 10/2015 | Cattaneo ............ A01J 5/007 119/14.08 |
| 2016/0319947 A1 | 11/2016 | Balkenhol |
| 2017/0014837 A1 | 1/2017 | Duke |
| 2017/0164576 A1 | 6/2017 | Balkenhol et al. |
| 2017/0359995 A1 | 12/2017 | Sellner et al. |
| 2018/0064056 A1 | 3/2018 | Torgerson et al. |
| 2018/0220616 A1 | 8/2018 | Torgerson et al. |
| 2018/0235173 A1 | 8/2018 | Torgerson et al. |
| 2019/0133067 A1 | 5/2019 | Stuessel et al. |
| 2019/0145531 A1 | 5/2019 | Balkenhol et al. |
| 2020/0088310 A1 | 3/2020 | Balkenhol |
| 2020/0352129 A1 | 11/2020 | Torgerson et al. |

FOREIGN PATENT DOCUMENTS

| | | | |
|---|---|---|---|
| AU | 2015227478 B2 | 3/2018 | |
| CA | 2394162 C | 8/2009 | |
| CA | 2772991 A1 | 3/2011 | |
| CA | 2772993 A1 | 3/2011 | |
| CA | 3016466 A1 | 3/2011 | |
| DE | 1801758 A1 | 6/1970 | |
| DE | 1582939 A1 | 7/1970 | |
| DE | 2622794 A1 | 12/1977 | |
| DE | 3540058 A1 | 5/1987 | |
| DE | 261300 A1 | 10/1988 | |
| DE | 4006785 A1 | 9/1990 | |
| DE | 10006548 A1 * | 8/2001 | ............ A01J 5/007 |
| DE | 10160161 A1 | 6/2003 | |
| DE | 102013114595 A1 | 6/2015 | |
| EP | 0277396 A1 | 8/1988 | |
| EP | 0313109 A1 | 4/1989 | |
| EP | 0319523 A2 | 6/1989 | |
| EP | 0332235 A2 | 9/1989 | |
| EP | 0459817 A1 | 12/1991 | |
| EP | 0479397 A2 | 4/1992 | |
| EP | 0527509 A2 | 2/1993 | |
| EP | 0543463 A1 | 5/1993 | |
| EP | 0583166 A2 | 2/1994 | |
| EP | 0630557 A2 | 12/1994 | |
| EP | 0728412 A1 | 8/1996 | |
| EP | 0801893 A2 | 10/1997 | |
| EP | 0945057 A1 | 9/1999 | |
| EP | 1001199 A2 | 5/2000 | |
| EP | 1219167 A2 | 7/2002 | |
| EP | 1222853 A2 | 7/2002 | |
| EP | 1089615 B1 | 3/2003 | |
| EP | 1520469 A1 | 4/2005 | |
| EP | 1543720 A1 | 6/2005 | |
| EP | 1790217 A2 | 5/2007 | |
| EP | 1795069 A2 | 6/2007 | |
| EP | 1679956 B1 | 12/2008 | |
| EP | 2113169 A1 | 11/2009 | |
| EP | 1933616 B1 | 1/2011 | |
| EP | 2277373 A2 | 1/2011 | |
| EP | 1737291 B1 | 11/2013 | |
| GB | 918766 A | 2/1963 | |
| GB | 1160900 A | 8/1969 | |
| GB | 1440901 A | 6/1976 | |
| GB | 0324647.7 | 10/2003 | |
| GB | 0402119.2 | 1/2004 | |
| GB | 0408968.6 | 4/2004 | |
| GB | 0417392.8 | 4/2004 | |
| GB | 2475249 A | 5/2011 | |
| JP | 2002345955 A | 12/2002 | |
| JP | 2002354958 A | 12/2002 | |
| JP | 2005192404 A | 7/2005 | |
| NL | 1016237 C | 3/2002 | |
| NL | 1021950 C | 5/2004 | |
| RU | 2084137 C1 | 7/1997 | |
| SU | 1676538 A1 | 9/1991 | |
| WO | 9313651 A2 | 7/1993 | |
| WO | 9828969 A1 | 7/1998 | |
| WO | 9927775 A1 | 6/1999 | |
| WO | 9946978 A1 | 9/1999 | |
| WO | 9966767 A1 | 12/1999 | |
| WO | 9966787 A1 | 12/1999 | |
| WO | 0117337 A1 | 3/2001 | |
| WO | 0117338 A1 | 3/2001 | |
| WO | 0207506 A1 | 1/2002 | |
| WO | 0223976 A1 | 3/2002 | |
| WO | 03030630 A1 | 4/2003 | |
| WO | 03077645 A1 | 9/2003 | |
| WO | 03098998 A1 | 12/2003 | |
| WO | 2004030445 A2 | 4/2004 | |
| WO | 2004032608 A1 | 4/2004 | |
| WO | 2005022986 A1 | 3/2005 | |
| WO | 2005043986 A1 | 5/2005 | |
| WO | 2005072516 A1 | 8/2005 | |
| WO | 2005102035 A2 | 11/2005 | |
| WO | 2006029797 A1 | 3/2006 | |
| WO | 2006091710 A2 | 8/2006 | |
| WO | 2006110079 A1 | 10/2006 | |
| WO | 2006117019 A1 | 11/2006 | |
| WO | 2006135917 A1 | 12/2006 | |
| WO | 2007031783 A1 | 3/2007 | |
| WO | 2007129884 A1 | 11/2007 | |

(56) References Cited

FOREIGN PATENT DOCUMENTS

| | | | |
|---|---|---|---|
| WO | 2007129888 | A1 | 11/2007 |
| WO | 2008102567 | A1 | 8/2008 |
| WO | 2008138862 | A2 | 11/2008 |
| WO | 2009077607 | A1 | 6/2009 |
| WO | 2009158000 | A1 | 12/2009 |
| WO | 2010053577 | A1 | 5/2010 |
| WO | 2011028292 | A2 | 3/2011 |
| WO | 2011028293 | A2 | 3/2011 |
| WO | 2011028294 | A2 | 3/2011 |
| WO | 2011102911 | A2 | 8/2011 |
| WO | 2014016588 | A1 | 1/2014 |
| WO | 2015118336 | A1 | 8/2015 |
| WO | 2015145116 | A1 | 10/2015 |
| WO | 2015150807 | A1 | 10/2015 |
| WO | 2017191057 | A1 | 11/2017 |
| WO | 2019090044 | A1 | 5/2019 |
| WO | 2019090136 | A9 | 5/2019 |

OTHER PUBLICATIONS

3-A® Accepted Practices for Permanently Installed Product and Solution Pipelines and Cleaning Systems Used in Milk and Milk Product Processing Plants, No. 605-04, Section N; Aug. 20, 1994.
"Grade A pasteurized milk ordinance" 2003 Revision; US Department Health and Human Services, Public Health Service; Food and Drug Administration.
"PCT/US06/023075—ISR & Written Opinion rec'd Oct. 16, 2006".
"PCT/US09/03770—IPRP and Written Opinion rec'd Jan. 13, 2011, and ISR rec'd Oct. 7, 2009".
Akam, D.N., "The Development of Equipment for the Mechanization of Manual Operations in Milking Machine," 17th Annual Meeting, National Mastitis Counsel, Inc., Feb. 21-23, 1978, pp. 417-426.
Amendments and Observations filed Oct. 24, 2016 by An Udder IP Company Ltd in the Opposition of EP Patent 1737291, 47 pages.
Amendments and Observations filed Oct. 25, 2016 by GEA Farm Technologies GmbH in the Opposition of EP Patent 1737291, 13 pages.
Dec. 8, 2016 EPO Communication; Details and minutes of the oral proceedings, Opposition of EP Patent 1737291, 13 pages.
European Patent Office Preliminary Opinion and Summons to Attend Oral Proceedings issued Jan. 18, 2016, Opposition of EP Patent 1737291, 12 pages.
European Search Report issued Aug. 13, 2014, EP Application No. 14159588.4, 5 pages.
European Search Report mailed Jan. 30, 2020 for European Application No. 19204875.9, 6 pages.
European Search Report mailed Oct. 13, 2017, for European Application No. 17171229.2, 6 pages.
European Search Report issued Sep. 24, 2015 for EP Application No. 15171008.4, 6 pages.
Feb. 4, 2019 Reply to Grounds for Appeal, Opposition of EP Patent 1737291, 32 pages.
German Search Report for DE Application No. 10 2016 108 300.3, Mar. 10, 2017, 7 pages.
Grindal et al., "Automatic application of teat disinfectant through the milking machine cluster" Journal of Dairy Research, 56:579-585 (1989).
International Preliminary Report on Patentability for International Application No. PCT/US2018/058897, mailed May 5, 2020, 10 pages.
International Preliminary Report on Patentability for International Application No. PCT/US2018/059041, mailed May 5, 2020, 12 pages.
International Search Report and Written Opinion from PCT/EP2014/077684, dated Apr. 10, 2015, 10 pages.
International Search Report and Written Opinion from PCT/US2011/00322, dated Dec. 20, 2011.
International Search Report and Written Opinion from PCT/US2018/058897, dated Feb. 25, 2019, 19 pages.
International Search Report and Written Opinion from PCT/US2018/059041, dated Mar. 8, 2019, 20 pages.
International Search Report for PCT/EP2017/060232, mailed Aug. 3, 2017, 2 pages.
Jul. 27, 2017 EPO Communication; State of the Opposition Procedure and Summons to Attend Oral Proceedings, Opposition of EP Patent 1737291, 10 pages.
Etter to Alex Ferguson from Jeffry W. Smith dated Dec. 22, 2006, 2pp.
Mar. 13, 2018 Letter from the Proprietor, An Udder IP Company Ltd, Regarding the Opposition Procedure for Opposition of EP Patent 1737291, 23 pages.
Mar. 20, 2020 Examination Report for Australian Application No. 2018211343, 7 pages.
Mar. 30, 2017 EPO Communication, State of the Opposition Procedure and Invitation to File Observations, Opposition of EP Patent 1737291, 10 pages.
May 17, 2018 EPO Communication; Details and minutes of the oral proceedings, Opposition of EP Patent 1737291, 9 pages.
May 31, 2018 Interlocutory Decision in Opposition Proceedings, Opposition of EP Patent 1737291, 49 pages.
Neijenhuis; et al., "Health of dairy cows milked by an automatic milking system; Effects of milking interval on teat condition and milking performance with whole-udder take off", Oct. 2003, 23 pages.
Notice of Opposition and Opposition brief for EP Patent 1737291, Filed on Aug. 26, 2014 by GEA Farm Technologies GmbH, 74 pages.
Nov. 10, 2016 EPO Communication re: the Proprietor, An Udder IP Company Ltd's request concerning the staying/postponement of the opposition proceedings, Opposition of EP Patent 1737291, 1 page.
Nov. 25, 2016 EPO Communication re: results of the oral proceedings, Opposition of EP Patent 1737291, 5 pages.
Oct. 15, 2020 Communication Regarding Oral Proceedings in Opposition to EP Patent 1737291, 10 pages.
Office Action dated Jan. 18, 2022 in related/corresponding RU Application No. 2020115267.
Office Action for U.S. Appl. No. 10/576,744 dated Jun. 3, 2010, 8pp.
Office Action for U.S. Appl. No. 11/652,372 dated Feb. 11, 2008, 14pp.
Office Action for U.S. Appl. No. 11/662,454 dated Aug. 16, 2010, 20 pp.
Office Action for U.S. Appl. No. 11/904,769 dated Feb. 20, 2008, 9pp.
Office Action for U.S. Appl. No. 12/712,787 dated Jun. 27, 2011.
PCT/GB04/004343—Written Opinion of ISA & IPRP rec'd Feb. 3, 2005, 5pp.
PCT/US09/006026—IPRP, Written Opinion of ISA & ISR rec'd Mar. 6, 2010, 9pp.
Preliminary Amendment for U.S. Appl. No. 10/576,744, filed Apr. 21, 2006, 16pp.
Preliminary Amendment for U.S. Appl. No. 10/576,744, filed Aug. 7, 2008, 10 pp.
Reply filed on Dec. 16, 2015 by GEA Farm Technologies GmbH in the Opposition of EP Patent No. 1737291, 75 pages.
Response filed by GEA Farm Technologies GmbH on May 29, 2017, Opposition of EP Patent 1737291, 5 pages.
Response filed by Udder IP Company LTD on Jun. 2, 2017, Opposition of EP Patent 1737291, 4 pages.
Response filed Feb. 2, 2015 by An Udder IP Company in the Opposition of EP Patent 1737291, 53 pages.
Office Action dated Jan. 24, 2024 in related/corresponding EP Application No. 18 804 853.2.
Sep. 27, 2018 Statement of Grounds for Appeal, Opposition of EP Patent 1737291, 29 pages.
Sep. 30, 2021 Minutes of the Oral Proceedings in Opposition to EP Patent 1737291, 4 pages.
Sheam; et al., "Reduction of bacterial contamination of teat cup liners by an entrained wash system," Veterinary Record (1994), 134, 450, 1p.

(56) References Cited

OTHER PUBLICATIONS

Thompson; et al. "The End-of-Milking Sequence and its Mechanization" 1976 Winter Mtg., Dec. 14-17, 1976, Animal Physiology and Genetics Inst., Beltsville, MD, 15pp.
U.S. Appl. No. 60/566,313, filed Apr. 29, 2004, J.R.J. Duke.
U.S. Appl. No. 60/566,314, filed Apr. 29, 2004, J.R.J. Duke.
U.S. Appl. No. 60/578,997, filed Jun. 12, 2004, Kevin L. Torgerson.
Wildbrett et al., "Über Reinigung und Desinfektion von Tanks" Materials and Corrosion 12(12):759-764. Nov. 1961.

\* cited by examiner

AUTOMATED TEAT DIP FLUID MANIFOLD

CROSS REFERENCE TO RELATED APPLICATION

This application claims the benefit of U.S. Provisional Application 62/581,526, filed Nov. 3, 2017, U.S. Provisional Application 62/581,514, filed Nov. 3, 2017, and U.S. Non-Provisional application Ser. No. 16/178,996, filed Nov. 2, 2018, the disclosures of which are incorporated by reference herein.

FIELD AND BACKGROUND OF THE INVENTION

The invention relates generally to dairy animal teat dip applicators, and more particularly to teat dip fluid manifolds that receive teat dip fluids, such as teat dips, water and air, from main supply lines and direct the teat dip fluids to individual teat dip applicators while protecting milk lines.

Dairy milking systems as they relate to the present invention include a cluster of teat cups, each of which is matched with a flexible teat cup liner that is attached to a teat of a dairy animal with a vacuum. Vacuum is applied in pulses between the shell and liner to facilitate movement of the flexible liner to milk the dairy animals. Milk flows from the dairy animal through each flexible liner and then through a milk tube to a milker unit collecting assembly, which collects milk from all of the animal's teats. This combination of elements is known as a milker unit and can be used to milk cows, sheep, goats and other dairy animals. Each milker unit is used to milk multiple animals so it must be sanitized, at least periodically, to prevent transmission of dirt and germs into the milk, and to help prevent transmission of diseases from animal to animal.

Milk from individual animals flows from each milker unit collecting assembly through milk tubes and into a milk line that receives milk from all of the milker units in the dairy. The milk is then chilled and stored in a milk tank. The milk lines and storage systems must not be contaminated with dirt, debris, chemicals, pathogens, or contaminated milk. In the event that milk being collected is from a sick dairy animal, or a monitoring system determines the milk is unsellable, the milk would be diverted to a "bad milk" line or a "calf milk" line for feeding to calves.

Traditionally, dairy animal teats have been prepared for milking by cleaning the teats before milking using sanitizing teat dips, and protecting teats after milking by applying protective teat dips. These dips are broadly categorized as "pre-dips" and "post-dips." Before automated systems were used, the pre-dips and post-dips were applied by dairy operators manually, with cloth wipes or specialized teat dip applicators. The teat dips were effective in cleaning and protecting teats from infection, but as automated milking systems came into commercial use, automated teat dip applicators were developed to realize the full benefit of automated milking.

Various types of automated (robotic) milking systems have been developed with automated systems for applying teat dip, air, and rinsing fluids (referred to herein as "teat dip fluids") applied and rinsed from the system in a manner that protects milk lines, and the milk therein, from being contaminated. Protecting milk lines and milk is mandated in the United States Food and Drug Administration's Pasteurized Milk Ordinance ("PMO"), Item 14r., for example, as well as other regulatory agencies throughout the world.

To protect milk lines in the United States, they should be separated from potentially contaminating fluids using at least two automatically controlled valves or a double seat mixproof valve, with a drainable opening to the atmosphere between the valves or valve seats (PMO Item 14r). This arrangement is referred to as "block-bleed-block," and protects milk lines from contamination even when the valves or valve seats fail by draining fluid through the opening (bleed) rather than allowing it to pass through both valves or valve seats. Various embodiments of block-bleed-block valves and valve arrangements are known and operate effectively. See for example: U.S. Pat. Nos. 8,342,125; 9,510,556; and 9,686,958.

Milk line protection systems can be complicated because pre-dipping and post-dipping require that teat dipping fluids be delivered in precise dosages and in a timely fashion to provide proper teat treatment, system cleaning, system timing, and milk line protection. Dosage valves for teat dips measure proper dosage quantities of teat dips and ensure that the doses are delivered under pressure and in proper sequence. Air can be used to "chase" the teat dip through the lines to overcome sluggishness due to friction in the lines and viscosity of the teat dip. Following teat dip application, the delivery system must be sufficiently cleaned and rinsed with water or other rinsing fluid, to sanitize equipment before subsequent milkings.

Further complicating teat dip delivery systems is the requirement that the teat dip, air, and rinsing fluids provided from main source lines must be accurately divided and delivered to each teat of the dairy animal. Typically, dividing dosages of teat dip fluids is performed through a teat dip fluid manifold that receives the fluids from one or more main supply lines and then divides the fluids into individual delivery lines. Given the short time durations in which teat dip must pass through the teat dip fluid manifold, providing adequate milk line protections can be challenging.

Further complicating teat dip fluid delivery systems is a desire to prevent cross-contamination of the various teat dip fluids. For example, water should not be allowed to contaminate teat dip before it is delivered to a teat because the dip can be diluted and possibly less effective. Conversely, teat dip should not be allowed to contaminate water and air lines, which could foul the system and require additional maintenance. Also, pre-dips should not be contaminated by post-dips, which could contain iodine or other antimicrobial composition that would then enter the milk lines during milking.

Thus, there is a need for a reliable teat dip fluid manifold that protects milk lines from contamination, and teat dip fluids from cross-contamination, while providing reliability and minimal maintenance.

SUMMARY OF THE INVENTION

An automated teat dip manifold in accordance with the present invention includes: an upstream fluid valve having a closed position and an open position; a galley in fluid communication with the upstream valve; a downstream valve in fluid communication with the galley, and the downstream valve has a closed position and an open position; and a pressure monitor in communication with the galley to sense galley pressure when the upstream valve is in the closed position and the downstream valve is in the closed position. The existence of galley pressure above a predetermined level is indicative of valve leakage and required maintenance. The galley may be formed in a housing, for example.

Further, the galley can be filled with air or rinsing fluids to test the pressure of these fluids by the pressure monitor. Failure to reach predetermined pressures could indicate that the source of these fluids is inadequate and in need of maintenance.

The upstream valve can be a two-position, three-way valve or a two-position, two-way valve. The upstream valve can define a vent when the upstream teat dip valve is in the closed position. This vent can be in fluid communication with other portions of the galley that can be monitored by the pressure monitor.

The upstream valve can define a vent when the upstream valve is in the closed position; and the automated teat dip fluid manifold further comprises: a check valve downstream from the vent to provide protection from cross contamination.

The automated teat dip fluid manifold can also include a pre-charge container disposed upstream from and in fluid communication with the upstream valve, and the pre-charge container defines a fluid compartment; and a pressure source to pressure feed fluid from the pre-charge container to the upstream valve and the downstream valve. The precharge vessel can be included in the galley to be monitored by the pressure monitor.

The automated teat dip fluid manifold can include a fluid drain to drain teat dip from a precharge vessel, for example.

The galley can also define an air vent to release pressure that would otherwise inhibit flow of teat dip fluids through the manifold.

The automated teat dip fluid manifold can be dedicated to either pre-dip teat dip fluids or post-dip teat dip fluids. Other embodiments of a teat dip fluid manifold in accordance with the present invention can dispense both pre-dip teat dip fluids and post-dip teat dip fluids. In these embodiments, valves can be added to protect from cross contamination of pre-dip fluids and post-dip fluids.

DETAILED DESCRIPTION OF THE INVENTION

Figure 1:
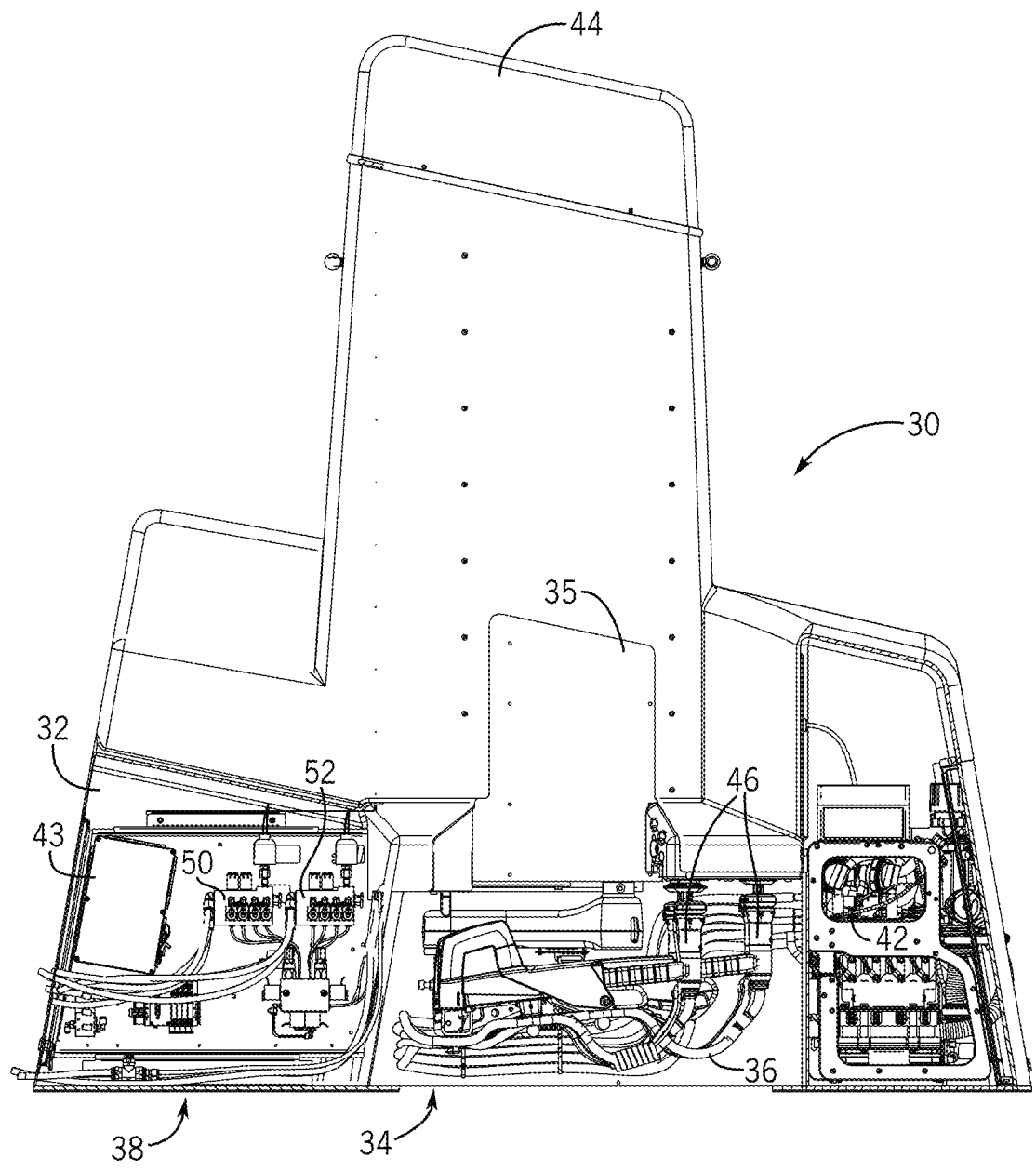
FIG. 1 is a side view of a dairy animal milking unit incorporating automated teat dip fluid manifolds in accordance with the present invention.

Illustrated generally in FIG. 1 is an automated dairy animal milking stall unit 30 used in a dairy harvesting facility. The dairy animal milking stall unit 30 can be used in any type of dairy arrangement, including those with stationary or rotary milking stalls, and the present invention is not limited for use in the particular type of milking stall unit 30 depicted herein.

The automated dairy animal milking stall unit 30 includes: a frame 32 for mounting in or adjacent to a milking stall; a milker unit 34 mounted in the frame 32; milk lines 36 as part of the milker unit 34; milker arm controls 35 used to control movement of the milker unit 34 between a parked position (shown) and a milking position (not shown); and a teat dip fluid supply system 38. Further, the frame 32 carries a milking module 42 for determining whether to direct milk to a "good milk" path, a "bad milk" path, or a "calf milk" path, for example. Also included, is a dipping module controller 43 that is programmed to monitor and control teat dipping, rinsing, and backflushing. The milking module 42 and the dipping module 43 are in communication with each other and coordinated by a programmable stall control 44, preferably concealed in an upper portion of the frame 32. It is preferred that all of the components described above be disposed in a single frame 32, but multiple frames or mounting systems can be used, so long as the teat dip fluid supply system 38 is in fluid communication with the milker unit 34 or at least a teat dip delivery unit for delivering pre-dip, post-dip, or both types of dip to a dairy animal's teats that will be milked using the milker unit 34.

The frame 32 can be open or enclosed or at least partially enclosed to protect the teat dip supply system 38, the milker unit control module 42, and the programmable stall control 44 from the harsh dairy environment and from being damaged by dairy animals.

The milker unit 34 can be of any suitable design and preferably includes teat cups and liner combinations 46, each of which receives an animal teat for milking. Generally, milk travels from the liner through the milk lines 36 and downstream to suitable chilling and storage systems.

Preferably, the milker unit 34 also carries one or more hoses and teat dip delivery nozzles or openings to direct teat dip toward each animal teat. Also, preferably, the teat dip delivery nozzles or openings are formed in a teat cup liner, examples of such liners are disclosed in Torgerson et al., U.S. Pat. No. 8,991,335, but other types of dispensers and/or liners can be used with the present invention.

Figure 2:
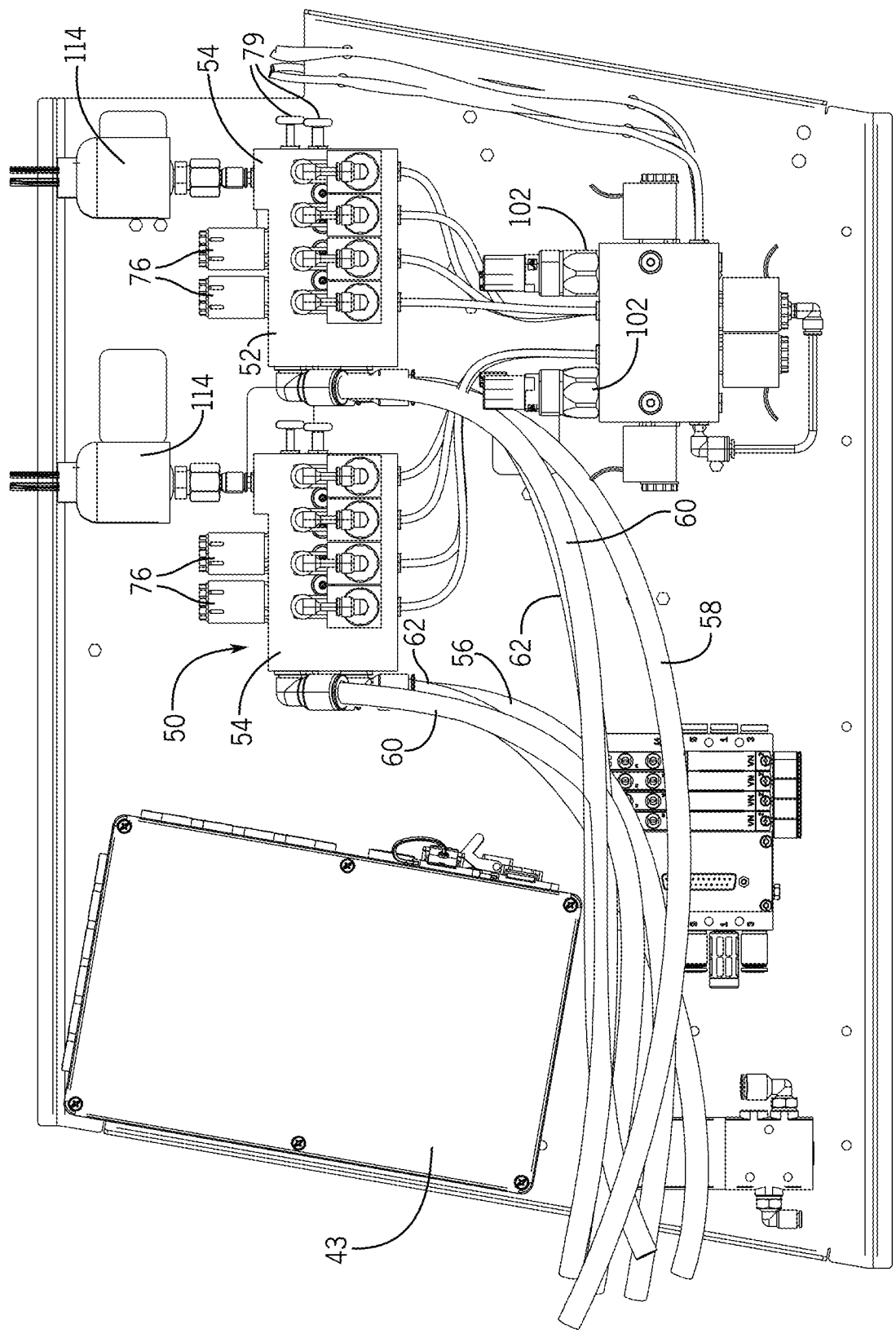
FIG. 2 is a side view of the teat dip fluid manifolds of FIG. 1.

To receive teat dip fluids such as teat dip, air, and rinsing fluids from appropriate sources and delivering them to individual dairy animal teats, the present invention includes at least one teat dip fluid manifold 50, and the embodiment depicted in FIGS. 1 and 2, includes a second teat dip fluid manifold 52. The first teat dip fluid manifold 50 delivers pre-dip fluids, and the second teat dip fluid manifold 52 delivers post-dip fluids. As described below, other embodiments of teat dip fluid manifolds can dispense both pre-dip fluids and post-dip fluids.

As used herein "teat dip fluids" can include teat dip for being applied before ("pre") or after ("post") milking, as well as, air to force teat dip through delivery lines, and rinsing fluids, such as water, for rinsing the teat dip fluid manifold, valves, delivery lines, and teat dip openings or nozzles. It is not necessary that all of these teat dip fluids be utilized in a single manifold 50, 52, but the present invention can be used to deliver one or more of these fluids effectively, efficiently, and reliably.

To simplify the following descriptions relating to FIGS. 1 to 6, only the first teat dip fluid manifold 50 will be described in detail, as the second teat dip fluid manifold 52 can have substantially the same construction or any other construction in accordance with the present invention. The teat dip fluid manifold 50 includes a housing 54, a teat dip supply line 56, an air supply line 60, and a rinsing fluid supply line 62. Other fluids can also be supplied to the teat dip fluid manifold 50, if desired. Further, the teat dip supply line 56 could be divided into two teat dip inlets, so that one receives pre-dip 56 and the other receives post-dip 58.

The teat dip fluids are then delivered to individual dairy animal teats through a number of delivery lines 68 (FIG. 7) that communicate from the teat dip fluid manifold 50 to a corresponding teat cup and liner combination 46.

Figure 3:
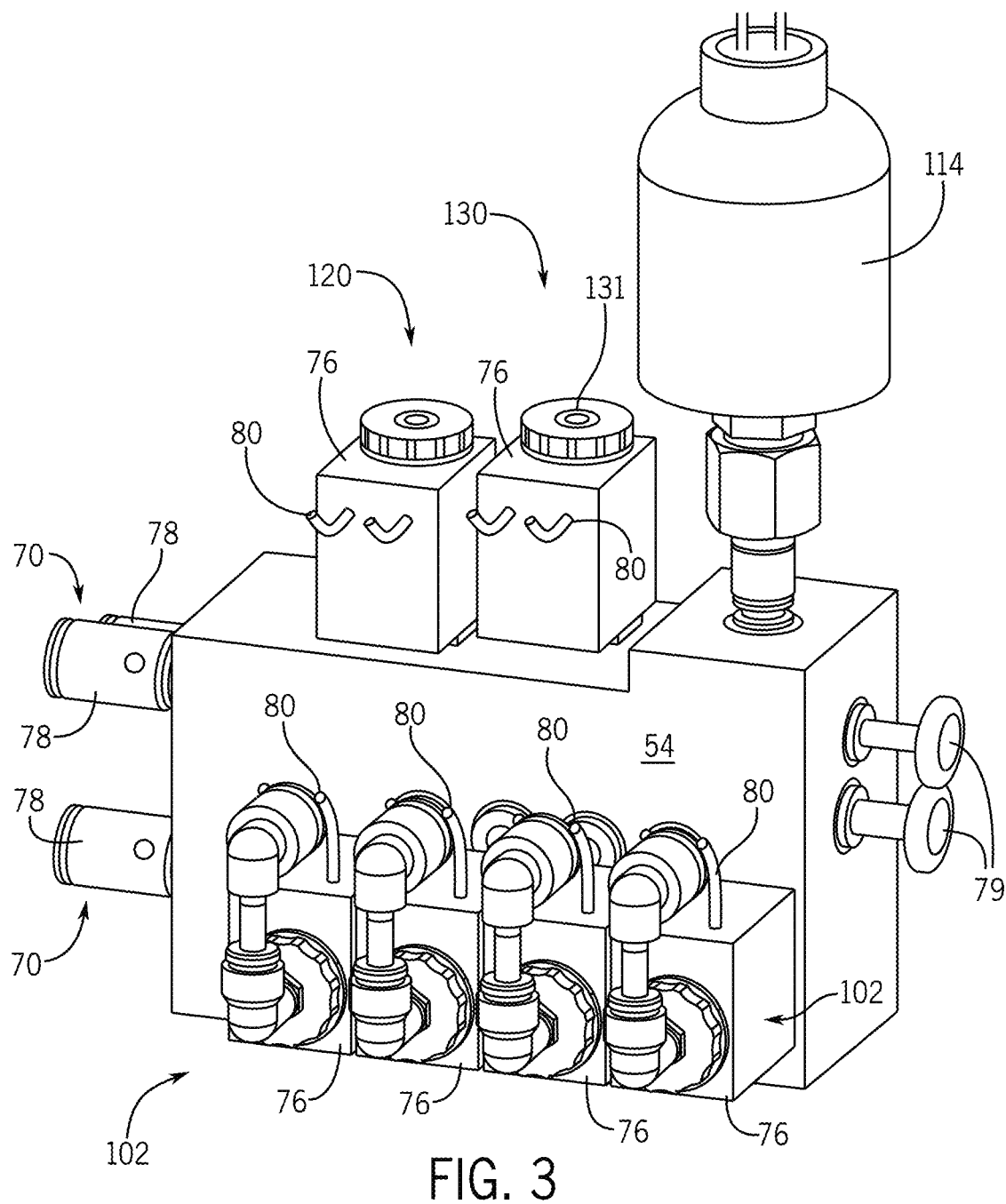
FIG. 3 is a perspective view of a teat dip fluid manifold in accordance with the present invention.
Figure 4:
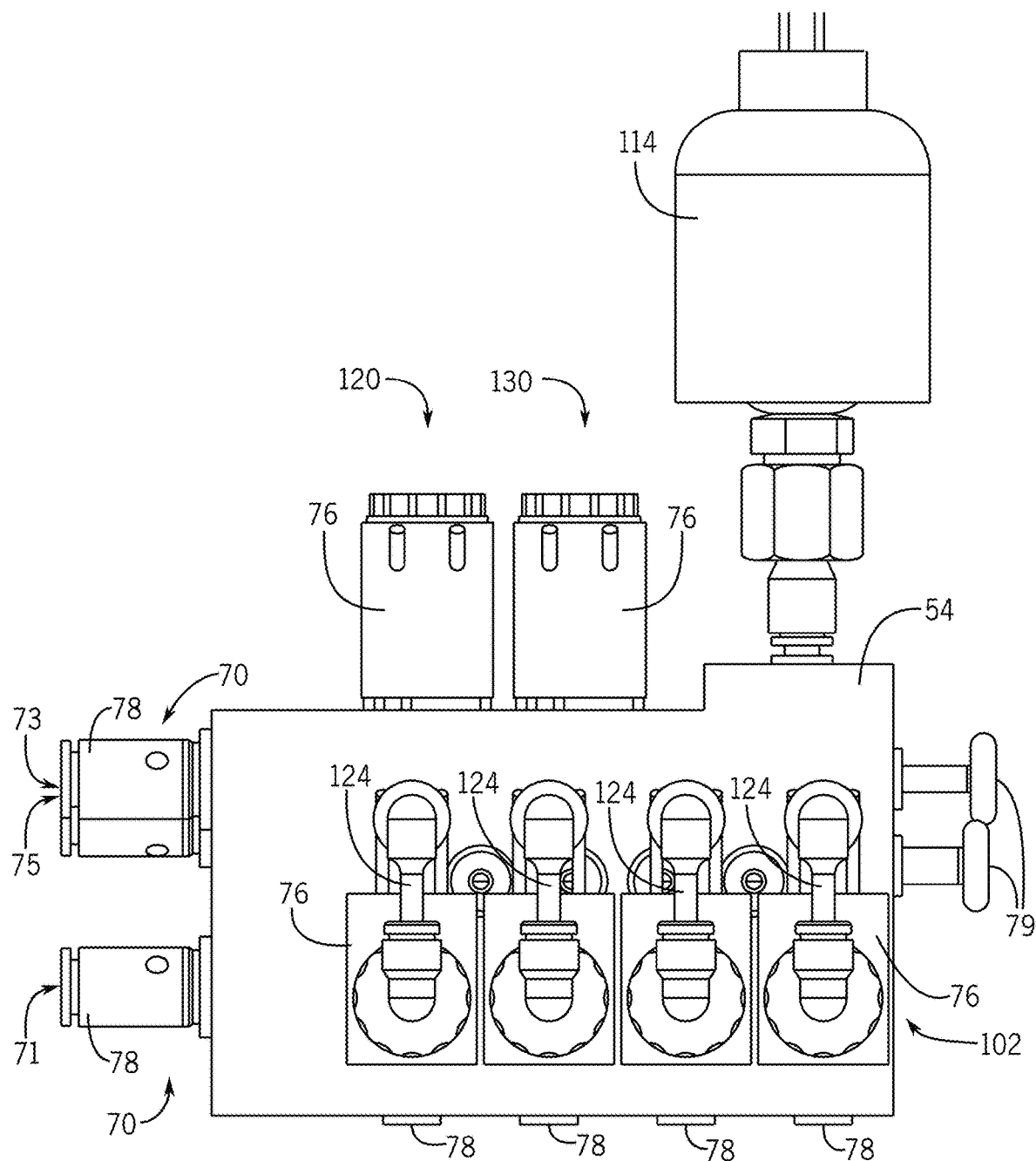
FIG. 4 is a front side view of the teat dip fluid manifold of FIG. 3.
Figure 5:
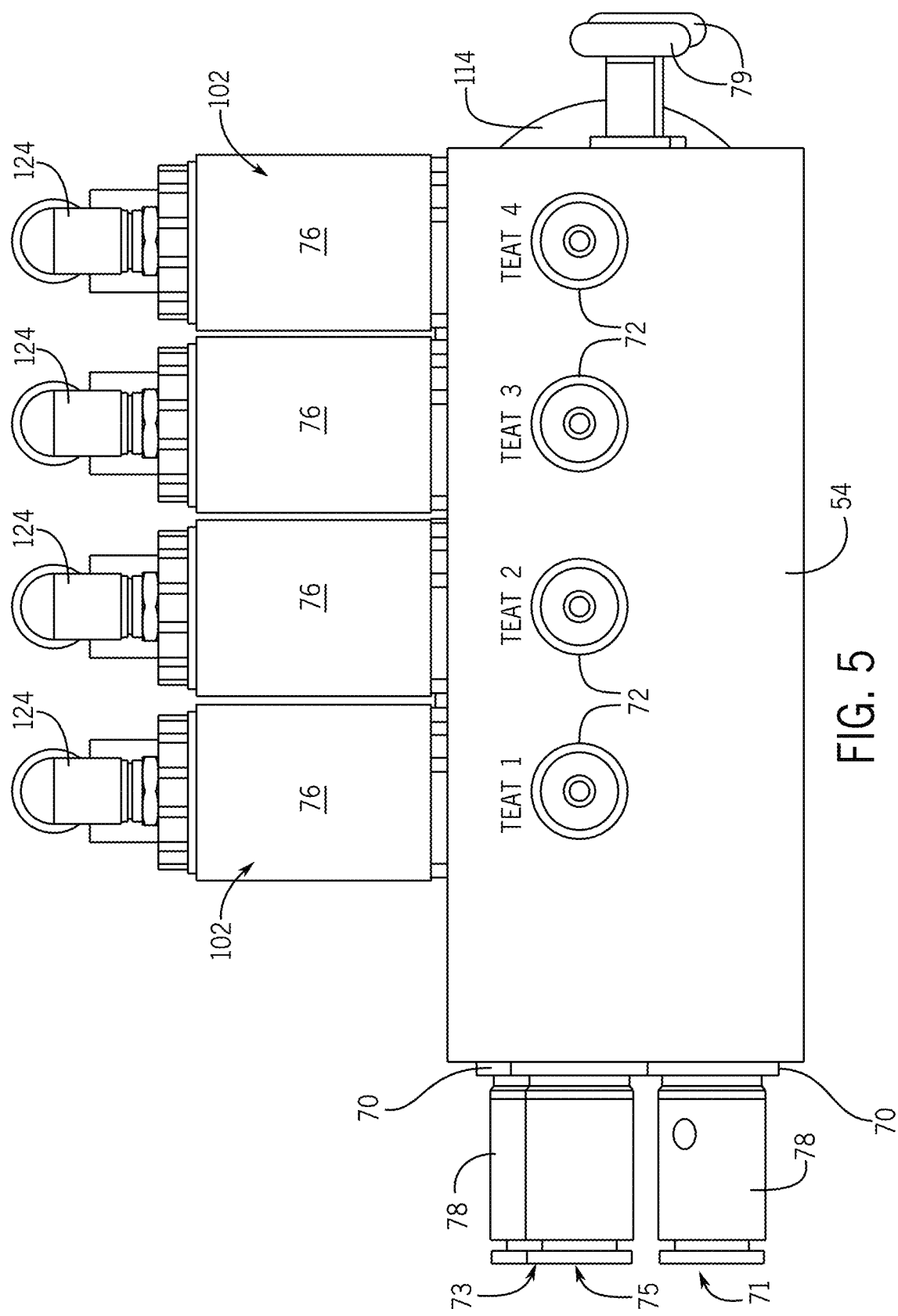
FIG. 5 is a bottom side view of the teat dip fluid manifold of FIG. 3.
Figure 6:
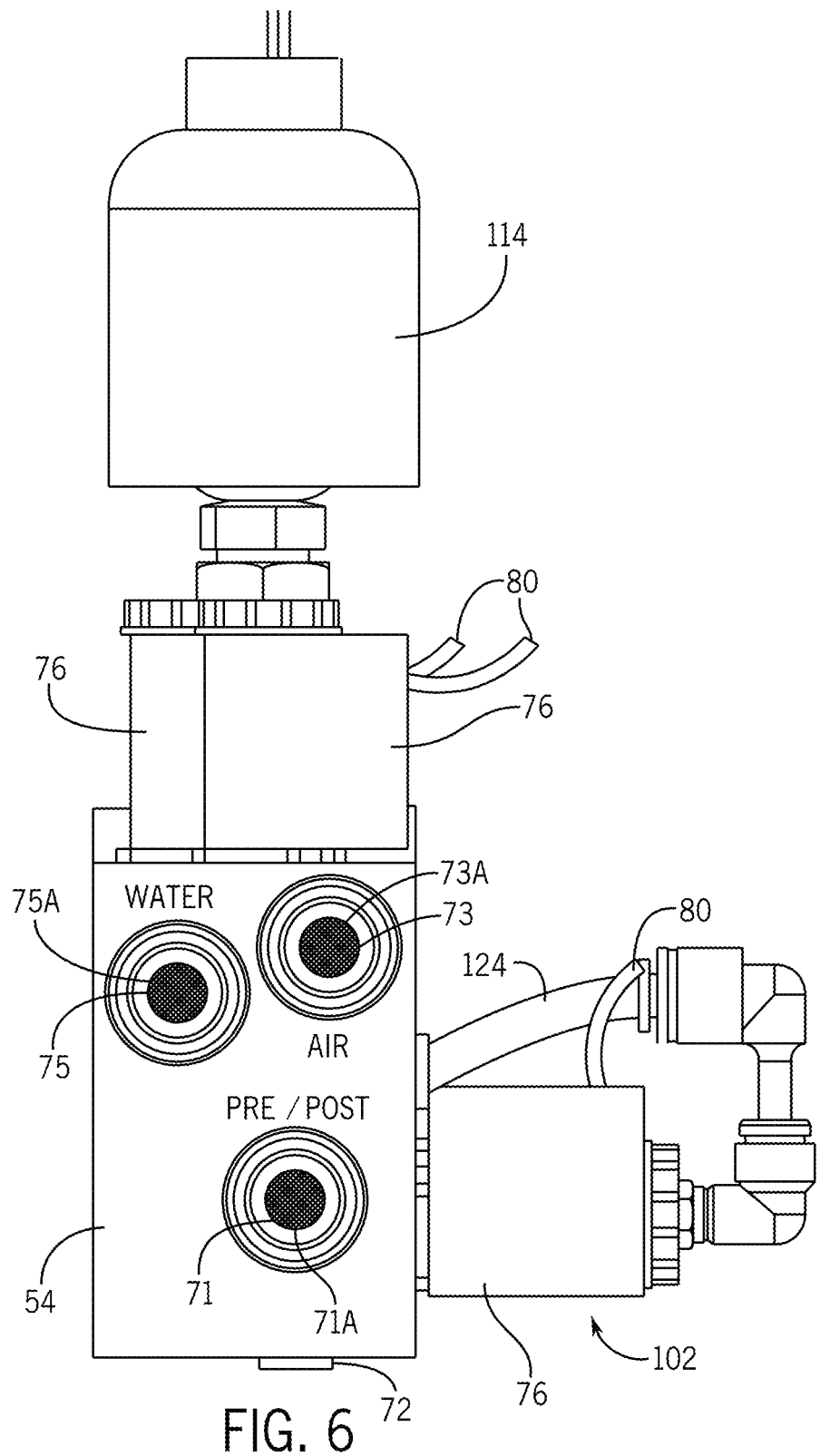
FIG. 6 is an end view of the teat dip fluid manifold of FIG. 3.

The housing 54 preferably includes inlets 70 (FIGS. 3, 4, 5), outlets 72 (FIGS. 4 and 5), and control valves 76 (FIGS. 3, 4, and 5, and described in more detail below). The housing inlets 70 and outlets 72 can be formed in the housing 54 using any appropriate method, and preferably include associated connectors or couplings 78 for connecting to supply lines 56, 58, 60, and 62, and delivery lines 68. Supply lines 56 and 58 can also serve as "pre-charge containers" for storing dip prior to being dispensed through the manifold 50.

The housing 54 is formed of any suitable material that can withstand the dairy environment as well as teat dips and rinsing fluids that pass through the housing 54. The housing 54 can be singular for containing most of the valve and seal components for use in either pre-dipping or post-dipping operations as described below in relation to FIG. 10, for example, or the housing 54 can be separated into multiple housings 54 in fluid communication with one another using any suitable device such as tubes, hoses, conduits, for example, or in direct fluid communication with the individual conduits 88 (FIG. 7) in which teat dip fluids pass to the teat cup and liner combinations 46. Housing vents 79 can be provided for access to internal components during manufacturing, for example.

An electrical power source 80 is also provided for powering valves and actuators within the teat dip fluid manifold 50, and computer controls may also be directly wired to the valves or power source for controlling valve operation. Wireless controls and interfaces can also be used.

Main supplies for teat dip, air, and water are preferably disposed at a central source location for convenience in supplying a number of teat dip fluid manifolds 50. Alternatively, supplies can be disposed at various stations in the dairy harvesting facility or even at individual milking stalls.

Teat dips, for example, can also be mixed on site or even as they are passing in the teat dip supply lines, 56, 58 with various ingredients, such as concentrates, water, or ingredients with short shelf lives.

Figure 7:
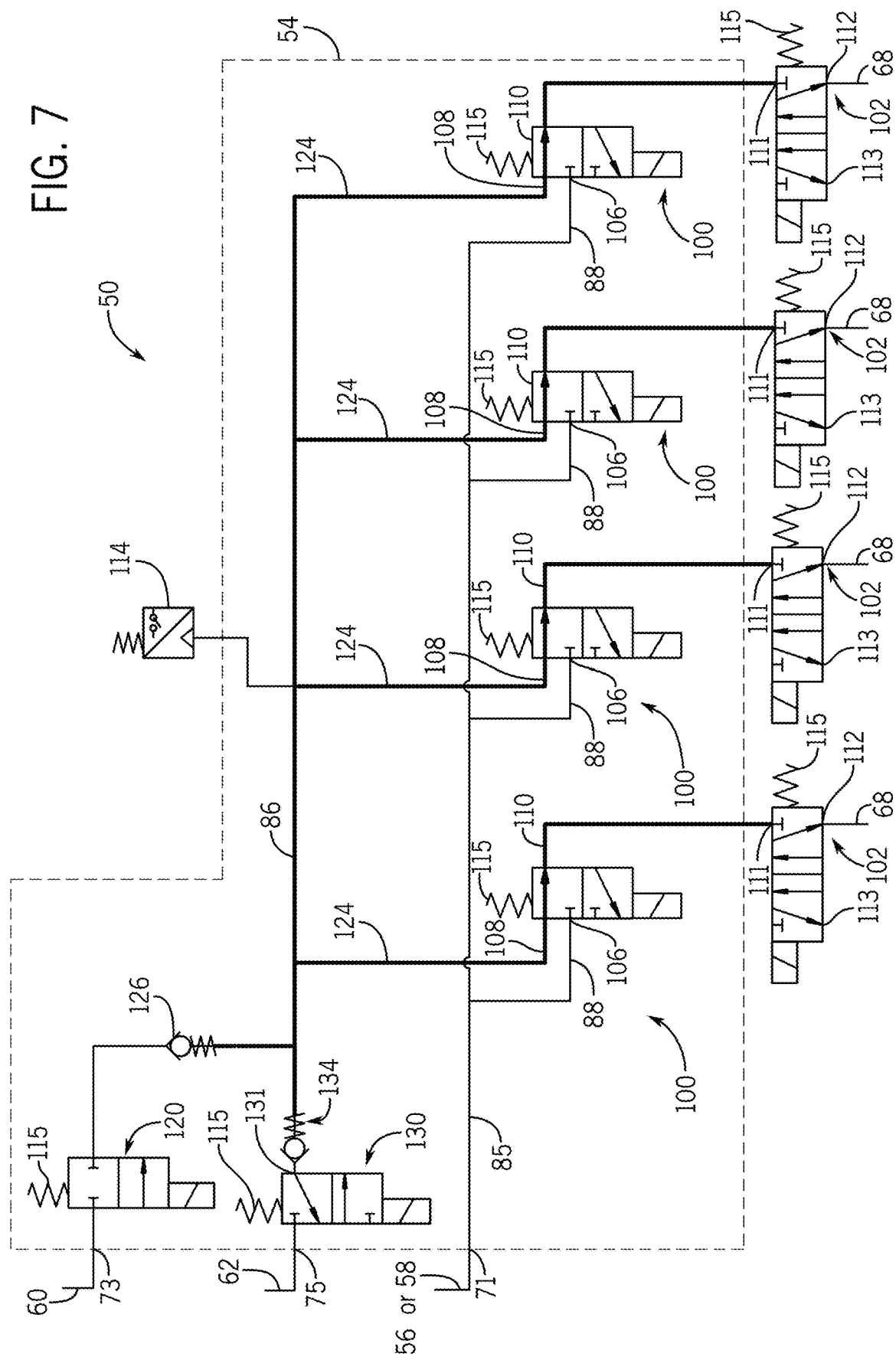
FIG. 7 is a schematic view of a first embodiment of a teat dip fluid manifold valve arrangement in accordance with the present invention.

FIG. 7 is a schematic illustration of a first embodiment of a teat dip fluid manifold 50 in accordance with the present invention. The teat dip supply line 56 (or 58 for a post-dip), the air supply line 60, and the rinsing fluid supply line 62 are illustrated in the upper left hand portion of the figure.

The teat dip supply line 56 connects to an inlet 71 protected by an optional mesh filter screen 71A (FIG. 6) and enters a main dip conduit 85, which is illustrated as a tube, but serves as a pre-charge container inside the housing 54, which includes branches of individual conduits 88 corresponding to each teat. Each individual conduit 88 preferably includes the same arrangement of valves, so only one set will be described. Teat dip fluid flow through each individual conduit 88 is controlled by an upstream valve 100 and a downstream valve 102. The individual conduits 88 are part of the main dip conduit 85 and terminate at the downstream valve 102 in the illustrated example. The upstream valve 100 in this embodiment is preferably a 2 position-3 way valve. As seen in FIG. 7, each 2 position-3 way valve includes a first inlet 106, a second inlet 108, and an outlet 110. The first inlet 106 receives teat dip, and the second inlet 108 can receive other teat dip fluids such as air and rinsing fluids, as described in more detail below.

The quantity of teat dip supplied to the teat dip fluid manifold 50 can be determined at an upstream location via a suitable dosage valve or it can be provided at a suitable back pressure, so that the upstream valve 100 can be opened for a predetermined interval to provide a desired quantity of teat dip while the upstream valve 100 is open.

Each downstream valve 102 is preferably a safety valve to provide added protection for milk lines in the dairy, but other types of valves can be used as well. The example of a downstream valve 102 illustrated is a safety valve and includes an inlet 111, an outlet 112, and a vent 113 disposed between the inlet 111 and the outlet 113 to create a block-bleed-bock arrangement.

The upstream valve 100 and the downstream valve 102 provide redundancy in protecting the milk lines from contamination from teat dip fluids. To add further protection, a galley 86 is provided from an air check valve 126 and a rinse fluid check valve 134, into and including individual conduits 124 extending to the downstream valve 102. Included in this example of the galley 86, is the passage through the upstream valve 100 from the second inlet 108 to the outlet 110. The galley 86 is monitored for pressure by a pressure monitor 114, which in conjunction with a controller 43, monitors pressure in the galley 86 when the upstream valve 100 is closed to teat dip at inlet 106, and the downstream safety valve 102 is closed to all fluids, except at the vent 113.

The individual conduits 124 of the galley 86 extend through the upstream valve 100 second inlet 108 down to the downstream valve 102. The positions of the upstream valve 100 and the downstream valve 102 are controlled by actuators 115 of any desired type including the solenoid valves illustrated in the figures. If the pressure rises or falls outside of a predetermined range, the pressure monitor 114 generates an appropriate signal that can send an alarm or other notice to a controller or a dairy operator indicating the abnormality. In such a case, the milking stall unit 30 can be taken out of service or the milk can be directed to a "bad milk" line, for example.

When the upstream valve 100 and the downstream valve 102 are both closed as described below, pressure inside the galley 86 can rise or fall if one of the valves is leaking. Even small or subtle leakage can be detected and indicate that valve maintenance is required. Of course, more catastrophic valve failures can be detected and the pressure monitor's 114 signal can send data to the controllers 43 and/or 44 to deactivate all or any portions of the teat dip delivery systems or even the automated dairy milking stall unit 30 itself. Preferably, the pressure monitor 114 senses pressures of about 15 psi, but any desirable pressure range can be selected.

The pressure monitor 114 is preferably a pressure switch that flips when it senses a certain pressure. Also preferably, the pressure switch is adjustable. Pressure sensors can also be used that monitor pressures at varying levels and rates.

This arrangement of a galley 86 and a pressure monitor 114 can monitor for valve leakage as described above, but it can also be used to check for unsatisfactory air or rinsing fluid supplies. This procedure preferably takes place when there is no milking operation occurring. The downstream valve 102 is closed and air or rinsing fluid are introduced into the galley 86 through their respective valves 120 or 130. If the air pressure or rinsing fluid pressure is insufficient to reach a pressure at which the pressure monitor 114 is set, then this is an indication that supply pumps or anything affecting fluid pressures require attention. The failure of air or rinsing fluid pressure to meet predetermined standards can raise an alarm or even be used by the controller 44 to cease operations at that milking stall unit 30 or cause milk obtained at that stall unit 30 to be redirected to a "bad milk" line, for example.

The air supply line 60 connects to the housing 54 at a port 73, and only requires controlling with an air valve 120, which is preferably, a 2 position-2 way pneumatic valve that is in fluid communication with the individual air conduits 124, which each communicate with a corresponding upstream valve 100. To prevent cross-contamination of the air supply line 60 by other teat dipping fluids, an air check valve 126 is provided downstream from the air valve 120. Air (or any other suitable gas or gas mixture) provided to the teat dip fluid manifold 50 is preferably delivered immediately after a teat dip is sent from the teat dip fluid manifold 50. The air provides a back pressure to force ("chase") the teat dip through delivery lines to ensure delivery of a complete dose of teat dip, as well as a timely delivery of teat dip in the precisely-timed operation of an automated dairy-milking system. A port mesh filter 73A is preferably used to prevent debris from entering.

Next, a rinsing fluid, such as water, can be delivered through a port 75 (with a preferred mesh filter 75A) from the rinsing fluid supply line 62 through a rinsing fluid valve 130, which is preferably a 2 position-3 way hydraulic valve to provide a block-bleed-block arrangement between the rinsing fluid supply line 62 and the rest of the teat dip fluid manifold 50 using a vent 131. The rinsing fluid valve 130 preferably shares the individual air conduits 124 to delivery rinsing fluid through the rest of the teat dip fluid manifold 50 and the delivery lines 68. Nonetheless, separate individual rinsing fluid conduits could be used. Preferably, a rinsing fluid check valve 134 is provided downstream from the rinsing fluid valve 130 to prevent teat dip or air from cross-contaminating the rinsing fluid supply line 62.

In the embodiment of FIG. 7, when teat dipping is required, the controller 43 activates the upstream valve 100 inlet 106 to open and the downstream safety valves 102 to open to allow pressurized teat dip to flow from the teat dip supply 56, 58 through the conduits 88 and to the delivery lines 68. When a desired amount of teat dip has passed through the upstream valve 100, as determined by the period of time in which the upstream valve 100 is open for teat dip flow, the upstream valve 100 will be actuated to close to stop the teat dip supply 56, 58.

The upstream valve 100 inlet 108 will then be opened to the individual conduits 124 and the air valve 120 will be activated to open to supply pressurized air (or other gas) through each individual conduit 124, the upstream valves 100, the downstream valves 102 (which remain open from teat dip flow or are re-opened), and into the delivery lines 68 to "chase" the teat dip through the delivery lines 68 to the teats.

Once a desired amount of air is released, the air valve 120 closes, and the rinsing fluid valve 130 is activated to open to release rinsing fluid through the same path as the air traveled until a desired quantity of rinsing fluid has entered the system. Another activation of the air valve 120 could be used to "chase" the rinsing fluid through the system, if desired.

Once rinsing is complete, the rinsing fluid valve 130 and the air valve 120 are activated to be closed and the upstream valve 100 and the downstream safety valve 102 are activated to be closed. In this valve configuration, the teat dip fluid manifold 50 is in essentially a milking position because none of the teat dip fluids can reach the milk lines.

Further, in this milking position, the pressure monitor 114 monitors pressure levels in the galley 86 (heavy lines in FIG. 7), which includes individual conduits 124 and, as described above, generates data and/or warning signals if line pressure is outside of a desired or predetermined range, which might indicate that valve maintenance and/or replacement is necessary.

FIGS. 13A through 13E illustrate a teat dip manifold substantially as illustrated in FIGS. 3 through 7, except that many of the conduits are formed from tubes that are part of the housing 54. The teat dip fluid manifold 50 is depicted, (a second teat dip fluid manifold 52 would be substantially identical and can be used if separate manifolds were used for pre- and post-dips), including a housing 54 defining a teat dip inlet 71, an air inlet 73, a rinsing fluid inlet 75, which feed into the housing 54 conduits to a respective outlet 72, which in turn is connected to a delivery line 68.

Flow through the air inlet 73 is controlled by an air valve 120, and rinse fluid through the rinse fluid inlet 75 is controlled by a rinse fluid valve 130. Both air and rinse fluid flow through the galley 86 and the individual conduits 124 illustrated in FIG. 7, for example. Flow through each of the individual conduits 124 is controlled by an upstream valve 100 and a downstream valve 102.

A pressure monitor 114 is used to monitor pressure in the galley 86 and the individual conduits 124, and will send an appropriate signal to a controller, as described above, in the event pressure in the galley 86 is outside of a predetermined range. Such a signal would indicate the need for valve or system maintenance.

In this embodiment, the housing 54 can in the form of a frame and include a hanger feature 109 with hooks 113 for attaching to corresponding receivers in a mounting panel, such as seen in FIGS. 1 and 2.

Figure 8:
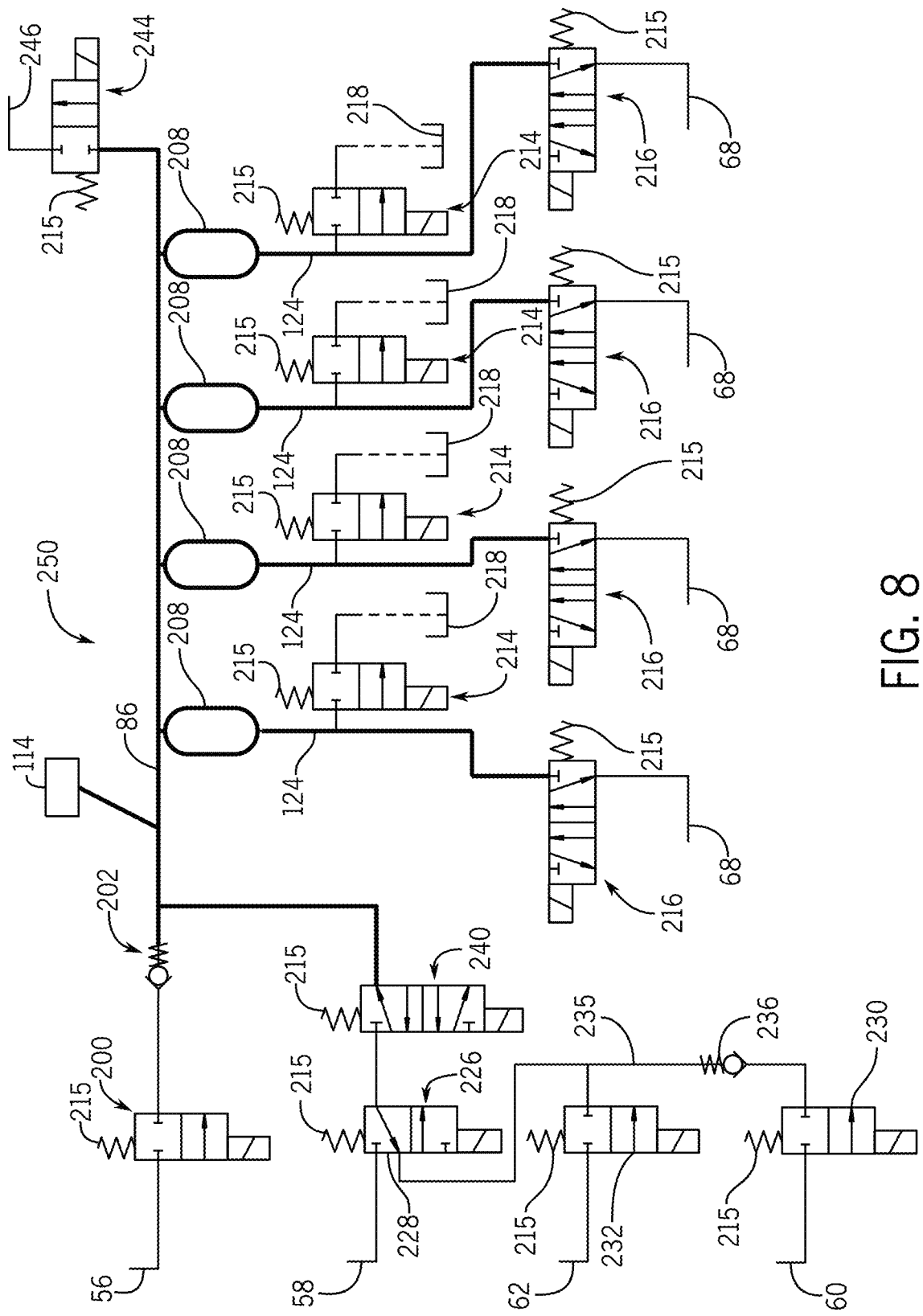
FIG. 8 is a schematic view of a second embodiment of a teat dip fluid manifold valve arrangement in accordance with the present invention.

In another embodiment illustrated in FIG. 8, a single teat dip fluid manifold 250 receives both pre-dip and post-dip, as well as air and rinsing fluid. In this embodiment, pre-dip teat dip is provided through the teat dip supply line 56, through a pre-dip valve 200, which is preferably a 2 position-2 way valve, but other valves could be used. Downstream from the pre-dip valve 200, is a pre-dip check valve 202 to prevent the pre-dip teat dip supply line 56 from being cross-contaminated by post-dip teat dip, rinsing fluids, and air. Pressurized teat dip is sufficient to open the check valve 202.

The pre-dip teat dip supply line 56 is in fluid communication with the galley 86 (bold lines) before splitting into the individual conduits 124. Each individual conduit 124 is provided with a pre-charging vessel 208 to provide a pre-measured dose of teat dip immediately upstream of a set of teat dip fluid manifold valves described below. This arrangement provides an immediate and accurately measured dose of teat dip or other teat dip fluid for delivery to a dairy animal teat or for rinsing the teat dip fluid manifold 250 and the delivery lines 68. Preferably, the pre-charging vessel 208 is sized to receive and store a pressurized volume of between four and eight milliliters (ml) of teat dip fluid, but other volumes or masses can be measured or metered to provide a desired quantity of teat dip.

Downstream from the pre-charging vessel 208 is a drain valve 214 and a downstream valve 216. The drain valve 214 is preferably a 2-position-2 way valve with a drain 218, so that teat dip can be drained from the related pre-charging vessel 208 in the event it is not needed for any reason. For example, all of the charging vessels 208 must be charged simultaneously. If one of the teats is re-dipped for some reason and only one vessel 208 is emptied for that re-dipping, then the other vessels 208 must be emptied through the drain valves 214. Although slightly wasteful, it provides a reliable means for re-dipping one or more teats, if necessary.

Each downstream safety valve 216 is preferably a suitable safety valve providing a block-bleed-block arrangement or a "block-monitor-block" arrangement as disclosed in U.S. patent application Ser. No. 62/581,514 entitled "Automated Milking System Safety Valve Arrangement," filed on Nov. 3, 2017, and naming inventors Matthew J. Stuessel, Wolfgang Schulze-Wilmert, and Thomas Orban, which is incorporated herein by reference.

A post-dip dip supply 58 is controlled by a post-dip valve 226 arranged in series with the air supply line 60 and the rinsing fluid supply line 62. Preferably, the post-dip valve is a 2-position-3 way valve for receiving post-dip, as well as, air and rinsing fluid through a separate valve inlet 228. Of course, other valve configurations can be used.

The air supply line 60 is controlled by an air valve 230, and the rinsing fluid supply line 62 is controlled by a rinsing fluid valve 232, each of which is preferably a 2-position-2 way valve. An air check valve 236 is provided downstream from the air valve 230 to prevent cross-contamination by teat dip and rinsing fluid.

To further isolate the post-dipping teat dip supply line 58 in the teat dip fluid manifold 50, a safety valve 240 is disposed downstream from the post-dip valve 226. This safety valve 240 can be any desired configuration, including a block-bleed-block or a block-monitor-block, as mentioned above.

Finally, the schematic FIG. 8 illustrates a vent valve 244 in the upper right portion that includes an air vent 246 for releasing pressure from the galley 86 while other fluids are entering. Venting the galley 86 lowers galley pressure to enable easier ingress of teat dip fluids into the manifold 50, 52. The galley 86 can be simply vented to atmosphere, or a vacuum could be applied to evacuate the galley 86 and even draw in teat dipping fluids, if desired.

As seen in FIG. 8, air and rinsing fluid are supplied in series to the post-dip valve 226 and pass through the post-dip valve 226 when that valve is activated to open to the water and an air line 235. This arrangement is efficient in terms of operation and space conservation.

Generally, when a milking operation is taking place, all of the valves are in closed positions, and an air pressure monitor 114 senses pressure in the galley 86, including the portions between the pre-charging vessel 208 and the downstream valve 216 for the purposes described above.

Before the milking operation, the pre-dip valve 200 is activated and pre-dip passes through the check valve 202 and the galley 86, and then is divided into each of the individual conduits 124 of the galley 86 to charge the pre-charging vessels 208. When pre-dip is desired, the downstream valve 216 opens and back pressure and air from the air valve 230 urge the pre-dip to pass through the delivery lines 68 to a teat cup and liner combination 46. Should all or a portion of the pre-dip fail to reach the teat cup and liner combination 46, the dip valves 200 or 226 can be activated to refill all of the pre-charging vessels 208, and only the teat or teats that did not receive dip can be re-dipped. Afterward, the pre-charging vessels 208 having unused teat dip therein can be dumped through a corresponding drain valve 214, so that all of the charging vessels 208 can receive the next teat dip fluid.

Subsequent to the pre-dip being passed through the manifold 250, an air "chase" passes through the air valve 230, the air check valve 236, the air line 235, the post-dip valve 226, the safety valve 240, the galley 86, and the rest of the path described above for the pre-dip.

Rinsing fluid can then be used, if desired, so that the rinsing fluid valve 232 will be activated to open and allow pressurized rinsing fluid to follow the same path as the "chase" air traveled, as described above.

Before milking is completed, post-dip can be released through an activated post-dip valve 226 and the valve 240, through the galley 86 and into the pre-charge vessels 208. This part of the process preferably can take place during milking or immediately following milking, but before the teat cup and liner combination 46 is detached from the dairy animal.

After milking and before detachment, the downstream safety valve 216 is activated to open and permit the post-dip to flow toward the teat cup and liner combination 46. Chase air and optional rinsing fluid can follow, as described above. Again, if post-dip fails to complete the delivery path, another dose can be provided, as described above in relation to the pre-dip teat dip. As illustrated, the valves include actuators 215.

Figure 9:
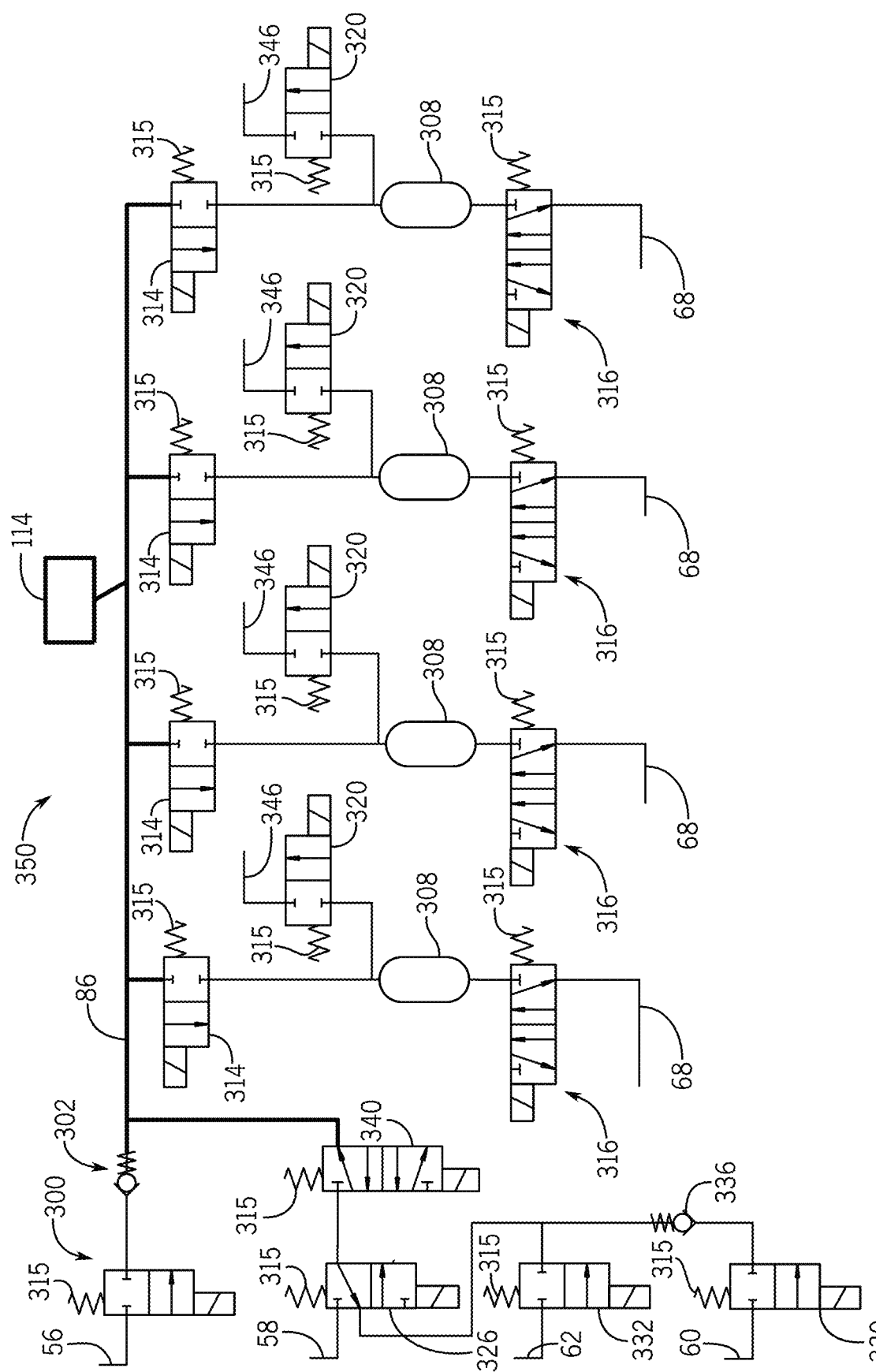
FIG. 9 is a schematic view of a third embodiment of a teat dip fluid manifold valve arrangement in accordance with the present invention.

A third embodiment is illustrated in FIG. 9, is similar to the second embodiment of FIG. 8, because it includes a manifold 350 with a similar arrangement of a pre-dip valve 300, and a pre-dip check valve 302.

One benefit of this embodiment is that the pre-charging vessel 308 can be refilled if for some reason it fails to fill completely, or the teat dip is delivered at a time when a teat is not located in a corresponding teat cup and liner combination 46. This refilling capability is less wasteful of teat dip compared to the FIG. 9 embodiment, but requires more valves. The ability to refill individual (versus all) charging vessels 308 results from the use of an upstream valve 314, and a second upstream valve 320 having an air vent 346, which vents the pre-charging vessel 308 and related lines to allow the pre-charging vessel 308 to be re-charged and applied to an animal teat: This process can be performed manually or automatically based on other sensors or observation made downstream from the manifold 350. As illustrated, the valves include actuators 315.

Downstream from the pre-charging vessel 308, is a downstream valve 316, which is preferably a safety valve such as a 2 position-5 way valve or a block-monitor-block valve.

In addition, as described above in relation to the second embodiment of FIG. 8, is a post-dip valve 326, an air valve 330, an air check valve 336, a rinsing fluid valve 332, and a safety valve 340, which all operate as described above.

The FIG. 9 embodiment wastes less teat dip, but requires more valves and results in the galley 86 not extending all the way to the downstream valves 316.

Figure 10:
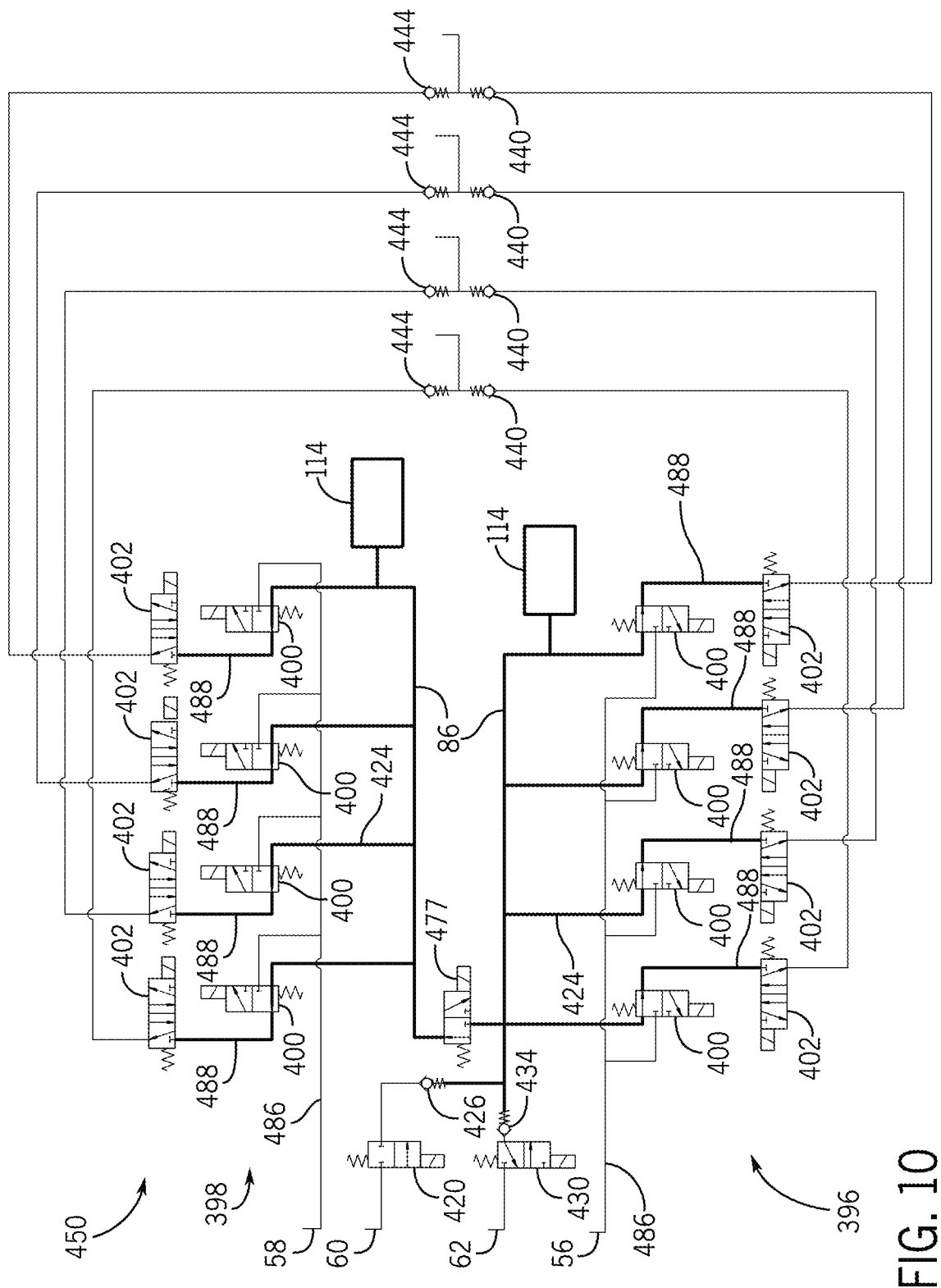
FIG. 10 is a schematic view of a fourth embodiment of a teat dip fluid manifold valve arrangement in accordance with the present invention.

In FIG. 10, a fourth embodiment is depicted, which is similar to the FIG. 7 embodiment, except that the teat dip fluid manifold 450 includes elements for dispensing both pre-dip teat dip fluids and post-dip teat dip fluids through a single housing 54. A pre-dipping portion 396 and a post-dipping portion 398 are provided, and they are both in communication with a single air supply line 60 and a single rinsing fluid supply line 62.

The pre-dipping portion 396 and the post-dipping portion 398 each include a galley 486 with individual conduits 488. In each individual conduit 488 there is an upstream valve 400 and a downstream valve 402. The upstream valves 400 are preferably 2 position-3 way valves for receiving teat dip through one inlet, and air and rinsing fluid through another inlet.

The other features of the first embodiment (FIG. 7) are also present, including: a pre-dip supply line 56; a post-dip supply line 58; an air supply line 60; a rinsing fluid supply line 62; an air valve 420; an air check valve 426; a rinsing fluid valve 430; and a rinsing fluid check valve 434. In addition, a pre-dip/post-dip selection valve 477 is provided to direct air and rinsing fluid to the pre-dip portion 396, when pre-dipping or to the post-dip portion 398, when post-dipping. A simple 2 position-2 way valve can be used for the selection valve 477. Again, actuators and valve position sensors are used in relation to any or all of the valves described above.

The individual conduits 488 of the pre-dip portion 396 are protected from cross-contamination from the post-dip portion 398, by a check valve 440 and the opposite is true because of the check valve 444. Other types of protective valves could be used as well to prevent cross contamination.

In this embodiment, a pressure sensor 414 is in fluid communication with each galley 486 to detect abnormal pressures in each galley 486, which could indicate leakage in any of the various valves, as described above.

Figure 11A:
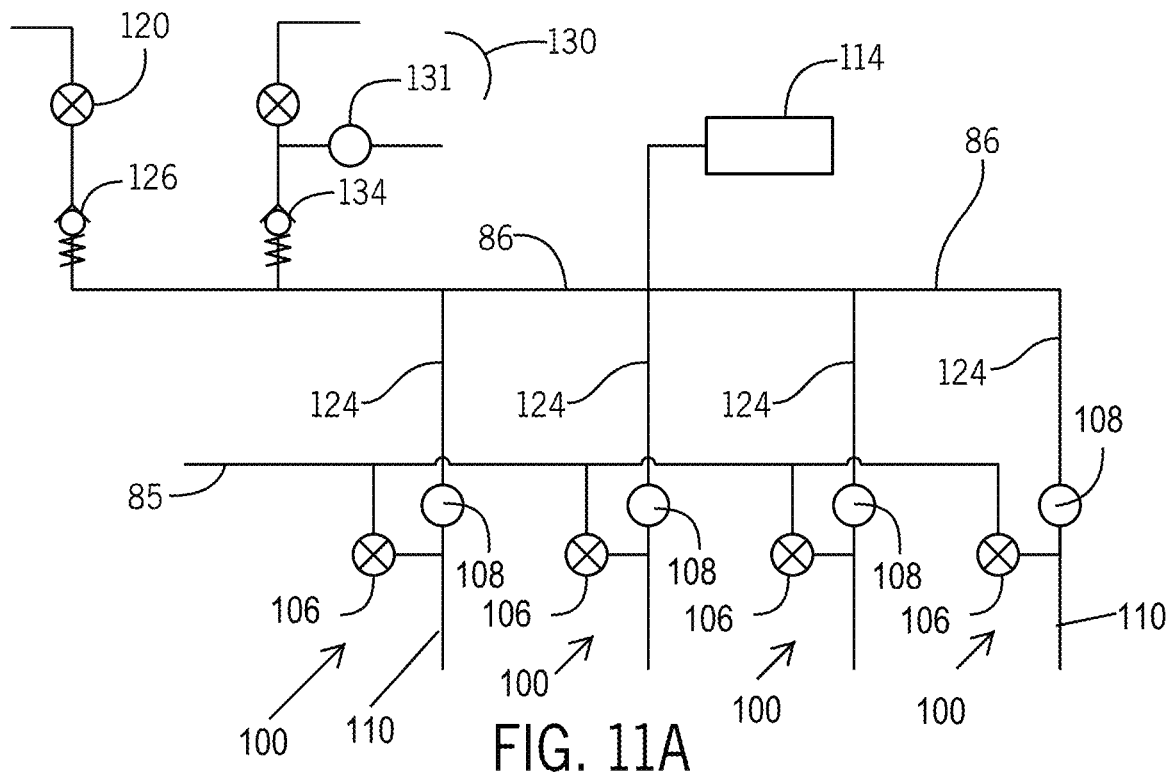
FIG. 11A through 11D are schematic views of a teat dip fluid manifold in accordance with the present invention, and each successive schematic illustrates a progression of valve positions for dispensing pre-dip teat dipping fluids.

FIGS. 11A to 11D illustrate a progression of valve positions that dispense pre-dip teat dipping fluids through a manifold 50, in accordance with the present invention. In FIG. 11A, the "good milk state", the upstream valves are closed and the downstream valves 102 (not illustrated in these figures) are also closed. The air valve 120 and rinsing fluid valve 130 are also closed. The galley 86, including the individual conduits 124 is monitored by the pressure monitor 114 for leaks. The individual conduits 124 are in communication with the rest of the galley 86 because the second inlet 108 and the outlet 110 in the upstream valve 100 are open to one another. (see: FIG. 7, for example.)

Figure 11B:
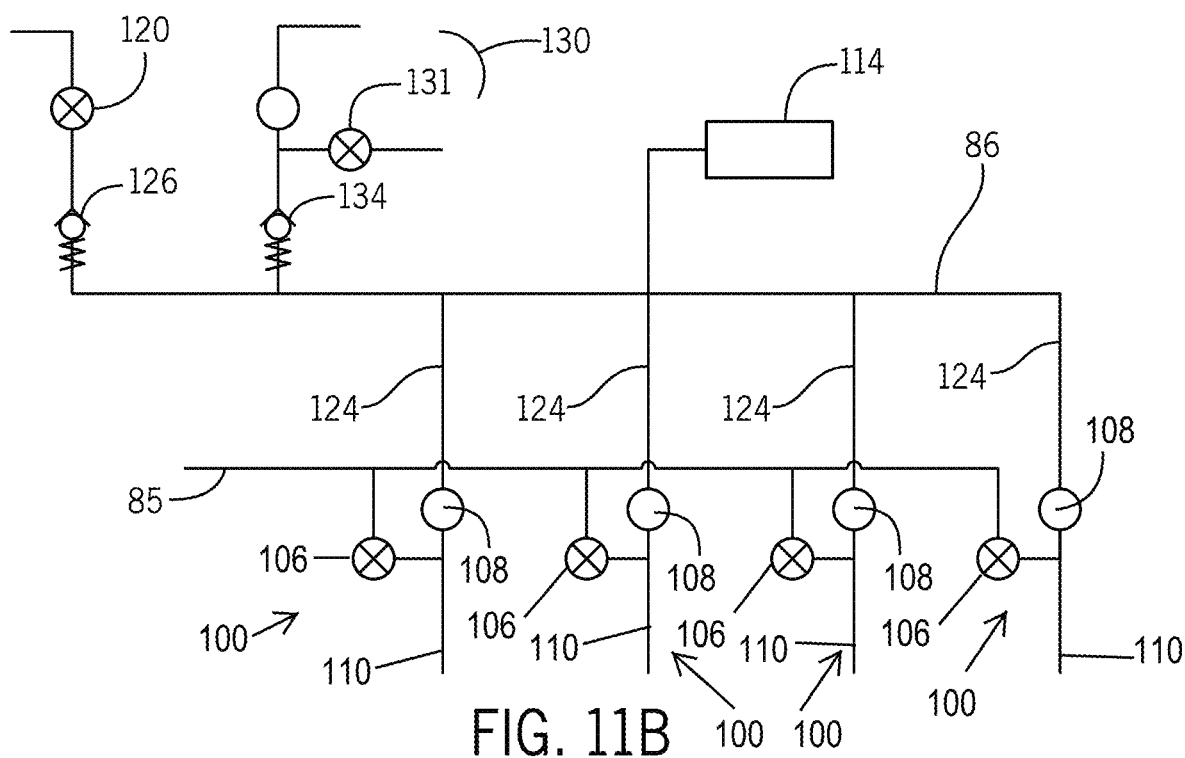

FIG. 11B illustrates the next step, "pre-cleaning," taking place by releasing rinsing fluid into the manifold 50. In this configuration, the rinsing fluid vent 131 is closed and the rinsing fluid valve 130 is opened to permit rinsing fluid to pass through the rinsing fluid check valve 134 and into the galley 86, including the conduits 124. The pressure monitor 114 can be used to check adequacy of the rinsing fluid supply, if desired.

Figure 11C:
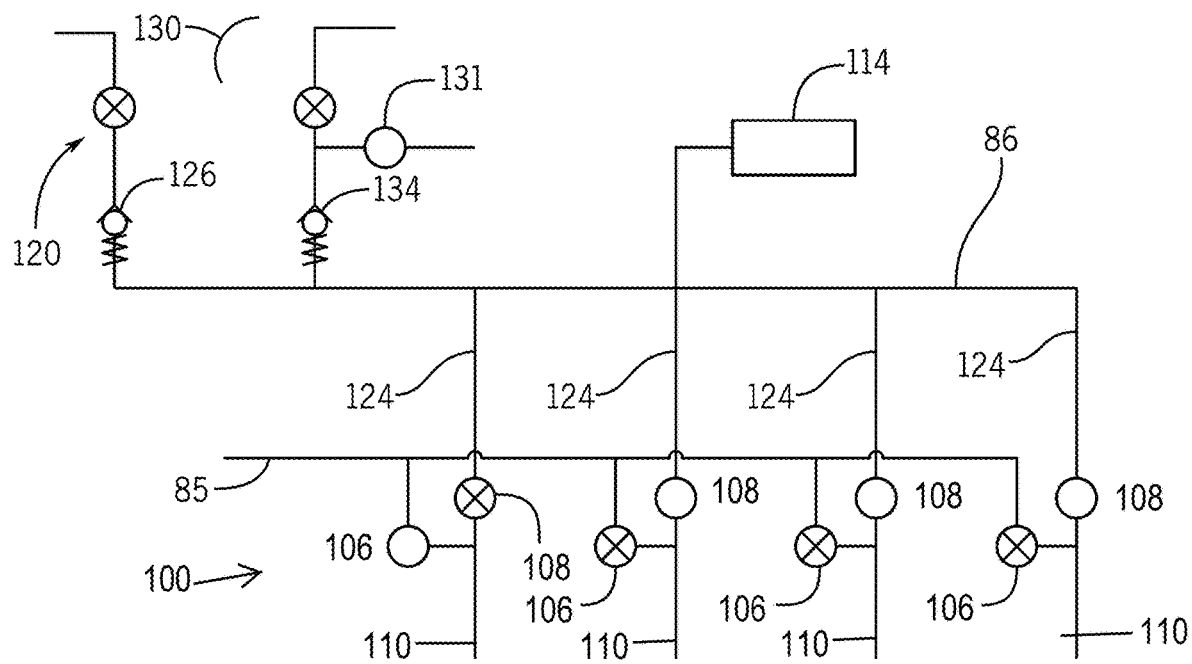

FIG. 11C illustrates the next step, "pre-dipping," during which the air valve 120 and the rinsing fluid valve 130 are closed. Pre-dip is provided through the pre-dip line 85, and in the illustrated example, only the first inlet 106 of the first upstream valve 100 and its corresponding downstream valve 102 (FIG. 7) are opened, and only an associated teat will receive pre-dip. This can occur while the other teats are being connected to the milking unit 34. Therefore, the first inlet 106 of the other upstream valves 100 remain closed until the other teats are attached.

Figure 11D:
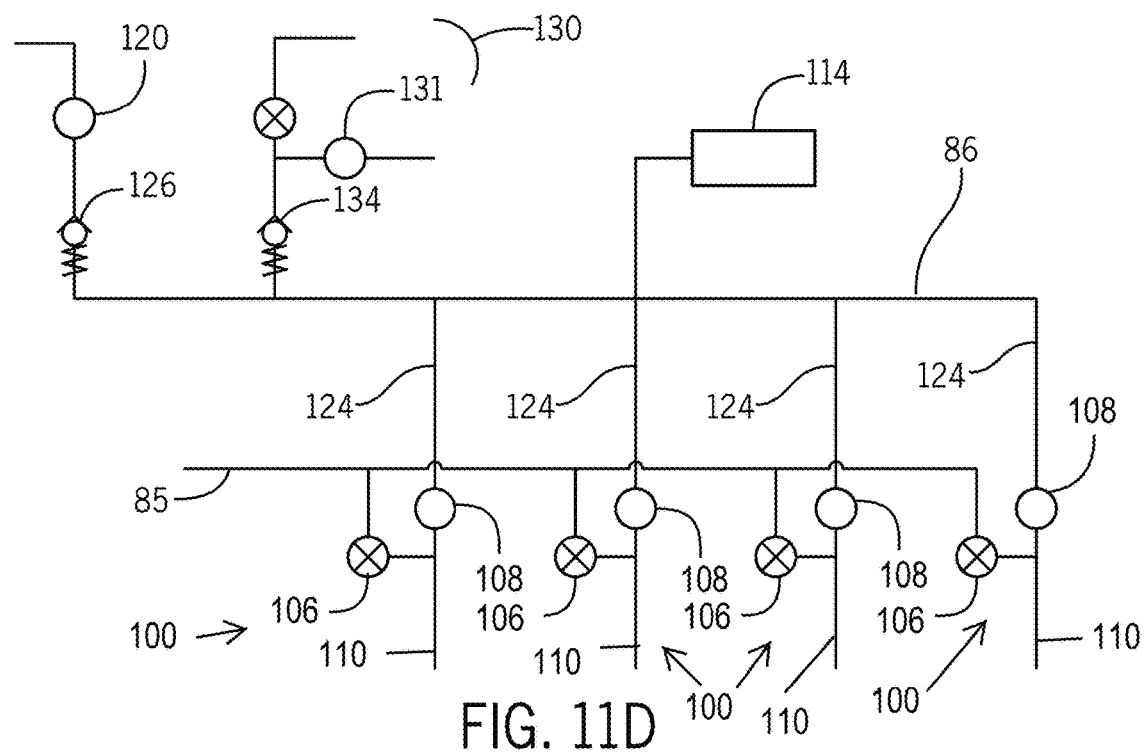

FIG. 11D illustrates the "dip chase" step in which the first inlet 106 of the upstream valves 100 are closed, but air and then rinsing fluid are allowed via the air valve 120 and the rinsing fluid valve 130, respectively, to enter the galley 86 and pass through the upstream valve second inlet 108 to 110 and through the downstream valves (again, not illustrated in this figure) and through the remaining flow path.

Figure 12A:
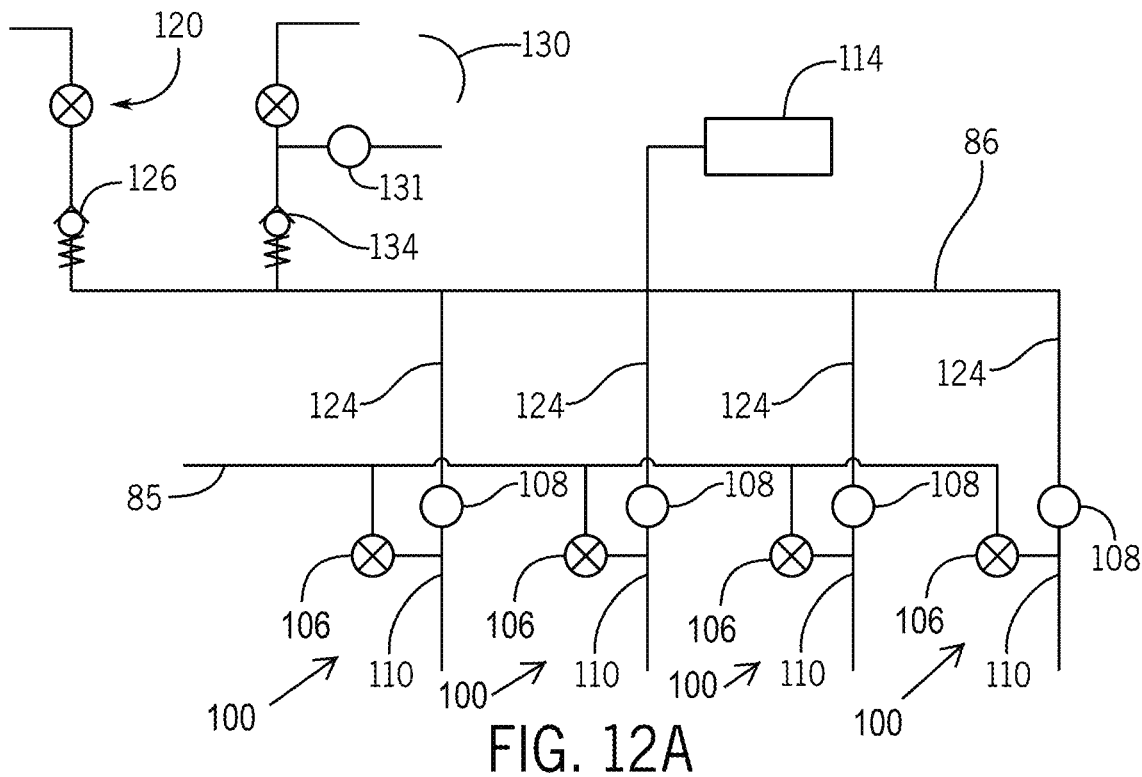
FIG. 12A through 12D are schematic views of a teat dip fluid manifold in accordance with the present invention, and each successive schematic illustrates a progression of valve positions for dispensing post-dip teat dipping fluids.

FIGS. 12A to 12D illustrate a progression of valve positions that dispense post-dip teat dipping fluids through a manifold 50, in accordance with the present invention. In FIG. 12A, the "good milk state", the upstream valves are closed and the downstream valves 102 (not illustrated in these figures) are also closed. The air valve 120 and rinsing fluid valve 130 are also closed. The galley 86, including the individual conduits 124 is monitored by the pressure monitor 114 for leaks. The individual conduits 124 are in communication with the rest of the galley 86 because the second inlet 108 and the outlet 110 in the upstream valve 100 are open to one another.

Figure 12B:
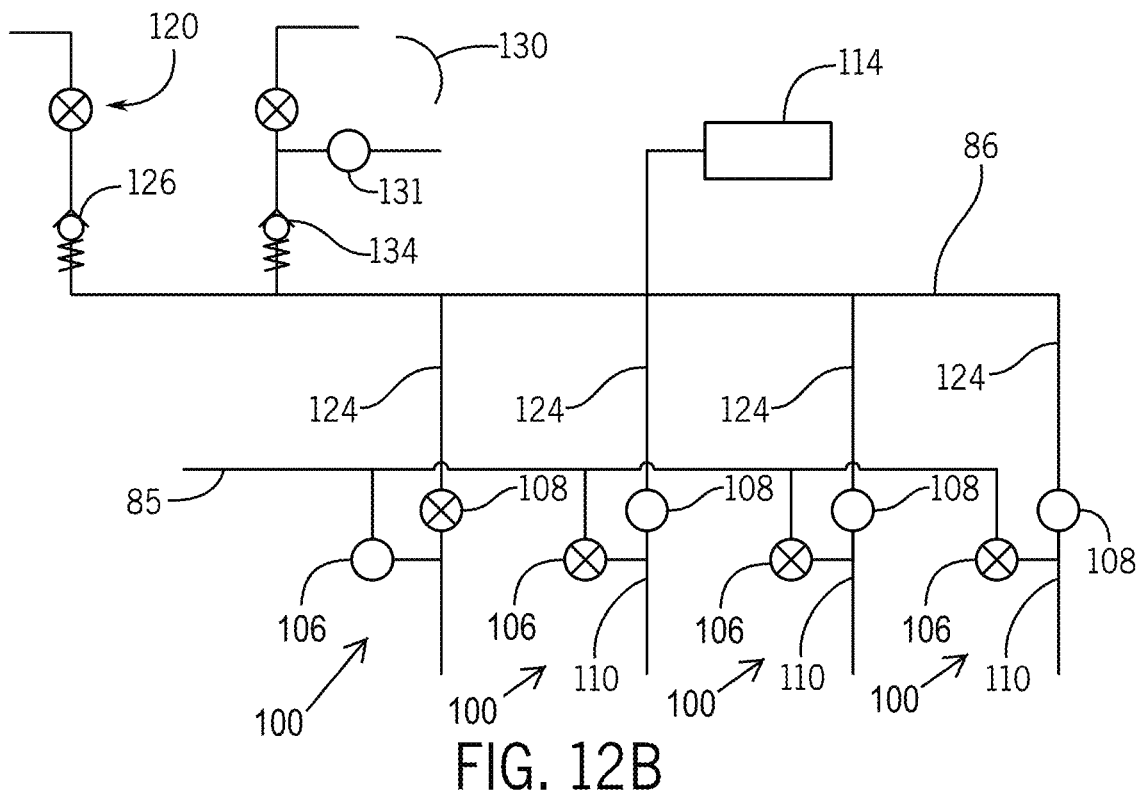

FIG. 12B illustrates the next step, "post-dipping," during which the air valve 120 and the rinsing fluid valve 130 are closed. Post-dip is provided through the post-dip line 85, and in the illustrated example, only the upstream valve 100 and its corresponding downstream valve 102 (FIG. 7) are opened, and only an associated teat will receive post-dip.

Figure 12C:
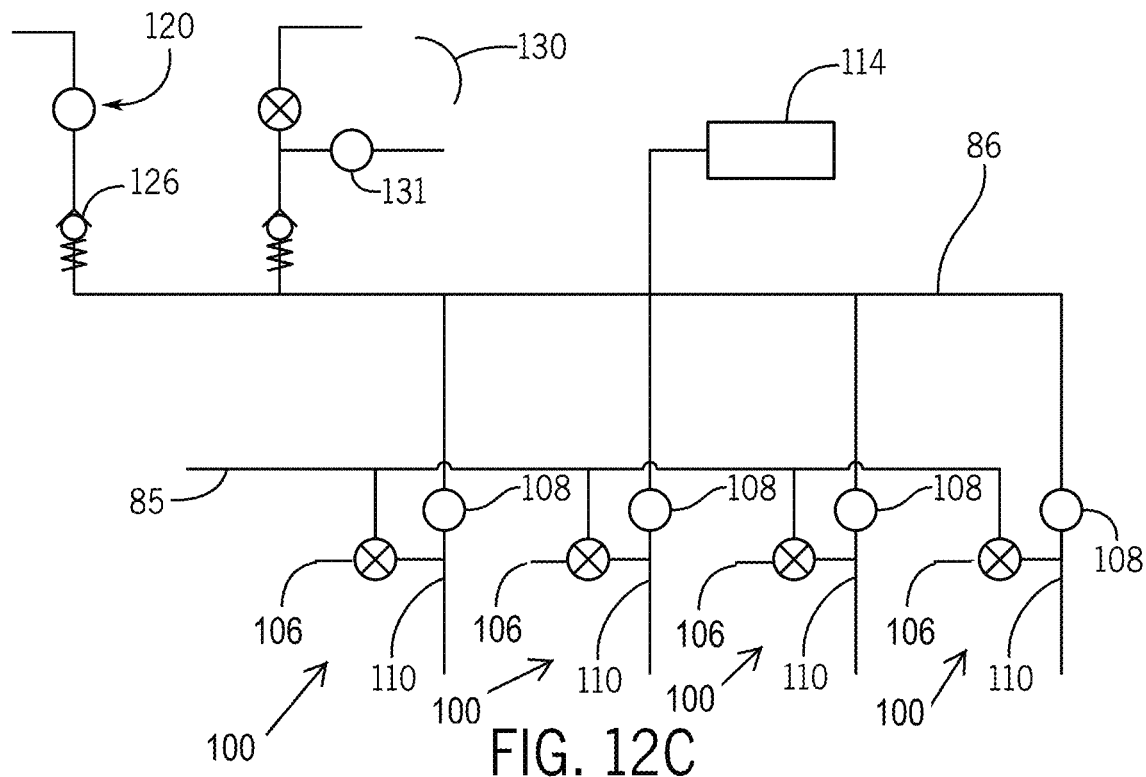

FIG. 12C illustrates the "dip chase" step in which the first inlet 106 of the upstream valves 100 are closed, but air and then rinsing fluid are allowed via the air valve 120 and the rinsing fluid valve 130, respectively, to enter the galley 86 and pass through the second upstream valve inlet 108 to the outlet 110 and through the downstream valves (again, not illustrated in this figure) and through the remaining flow path.

Figure 12D:
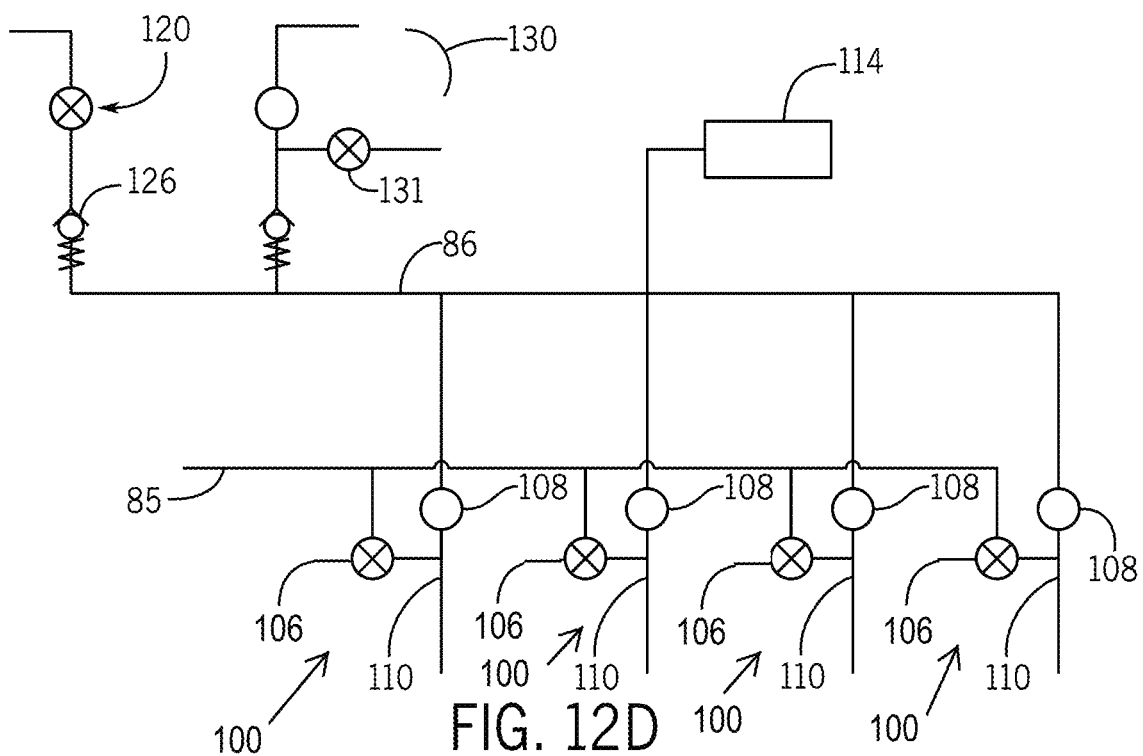
Figure 13A:
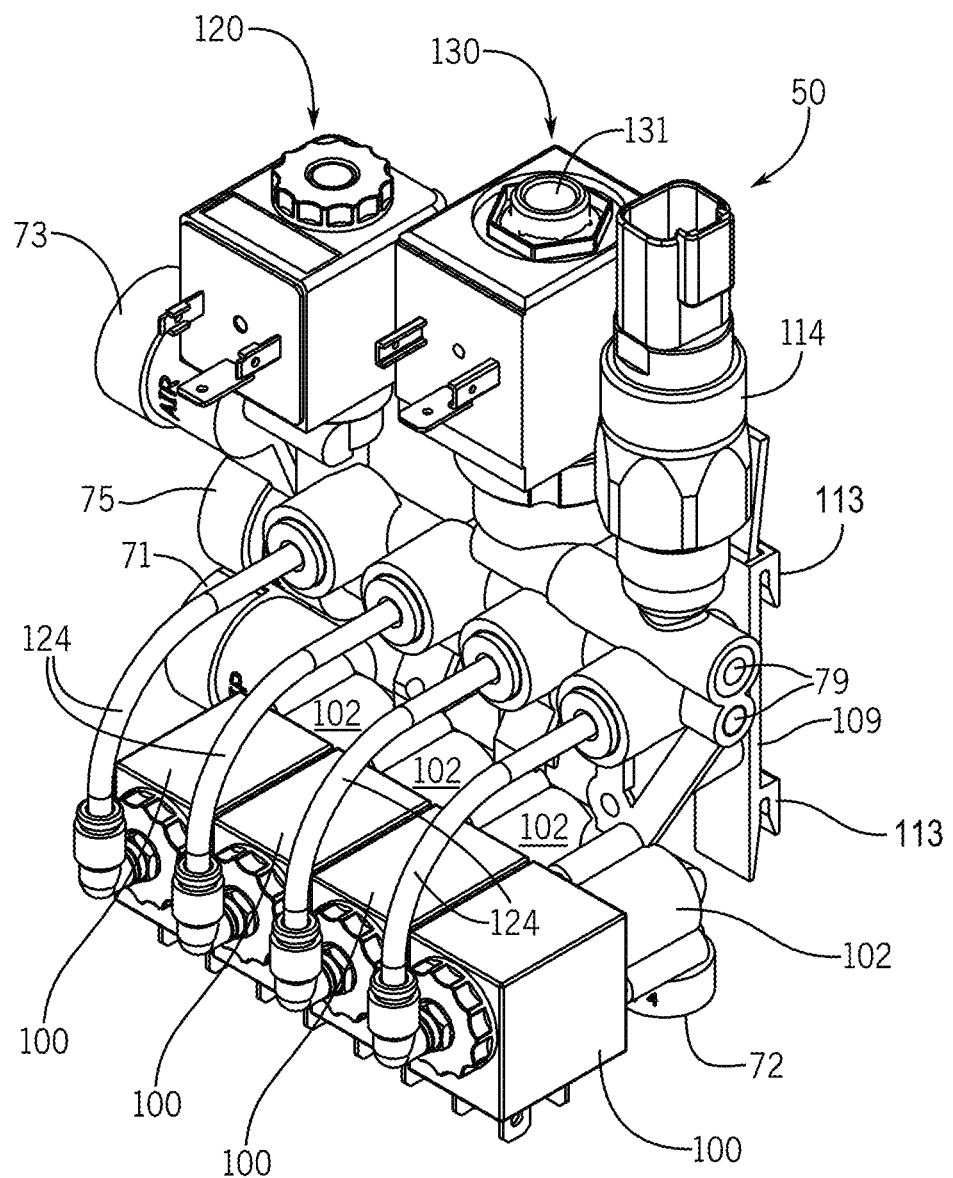
FIG. 13A is a perspective view of a teat dip manifold in accordance with the present invention.
Figure 13B:
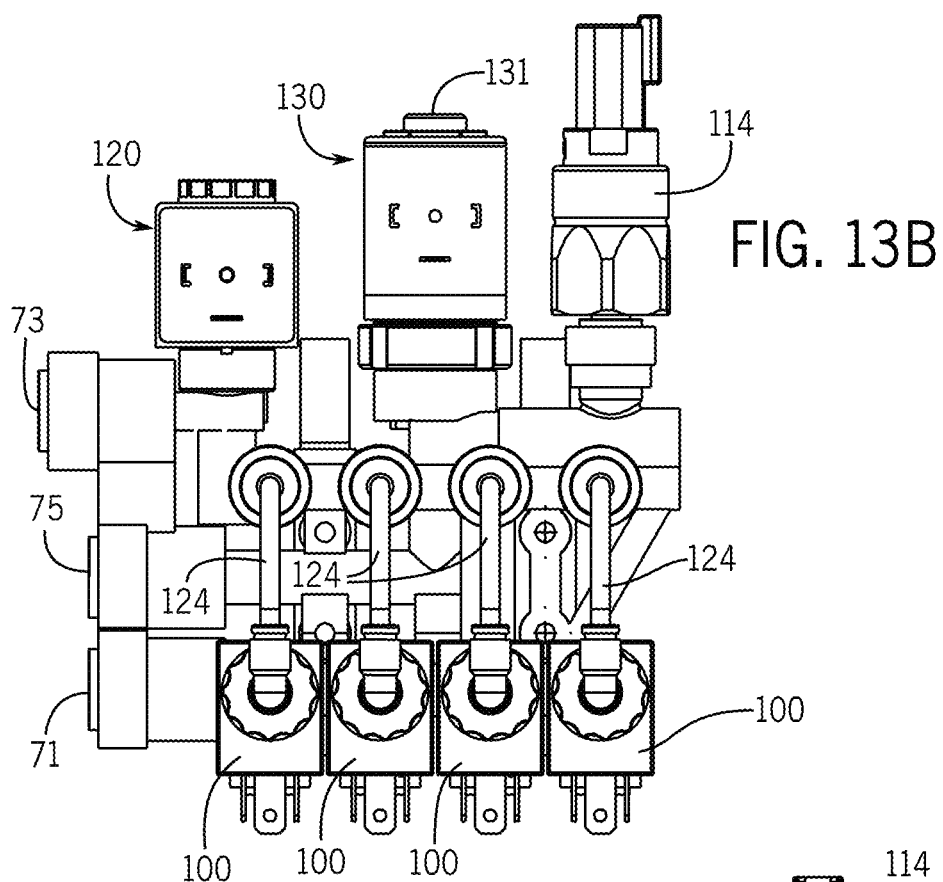
FIG. 13B is a front view of the teat dip manifold of FIG. 13A.
Figure 13C:
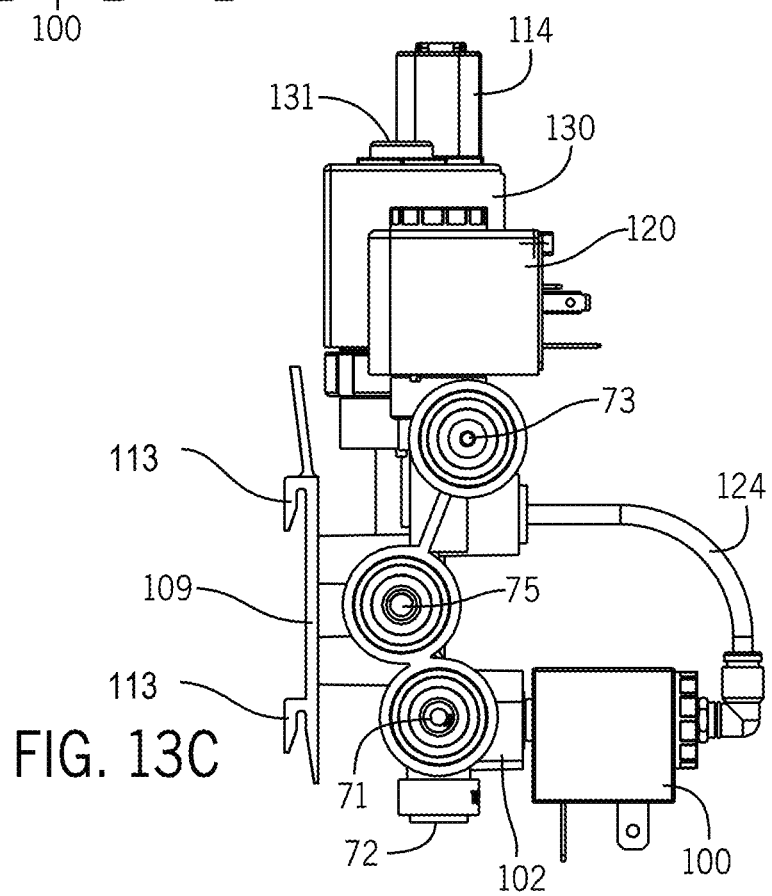
FIG. 13C is a right side view of the teat dip manifold of FIG. 13A.
Figure 13D:
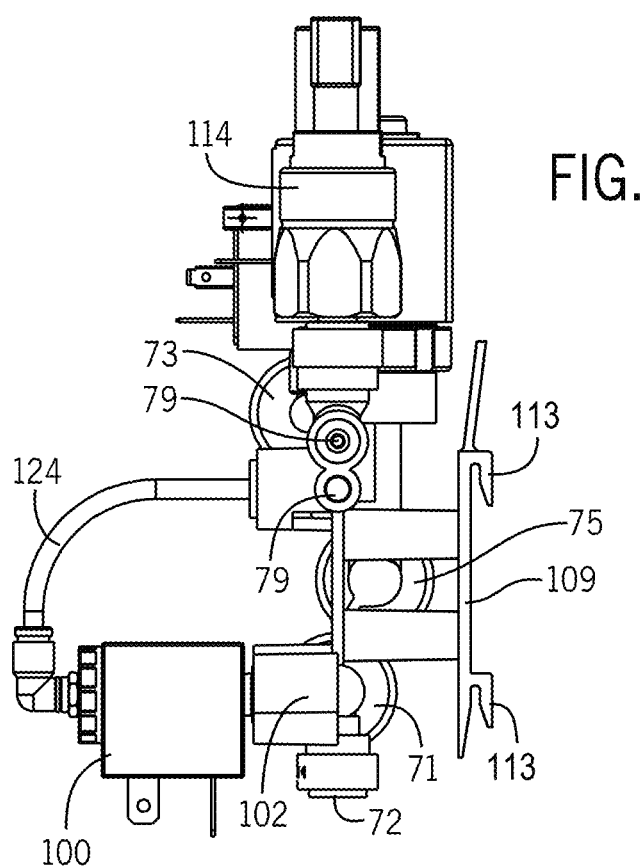
FIG. 13D is a left side view of the teat dip manifold of FIG. 13A.
Figure 13E:
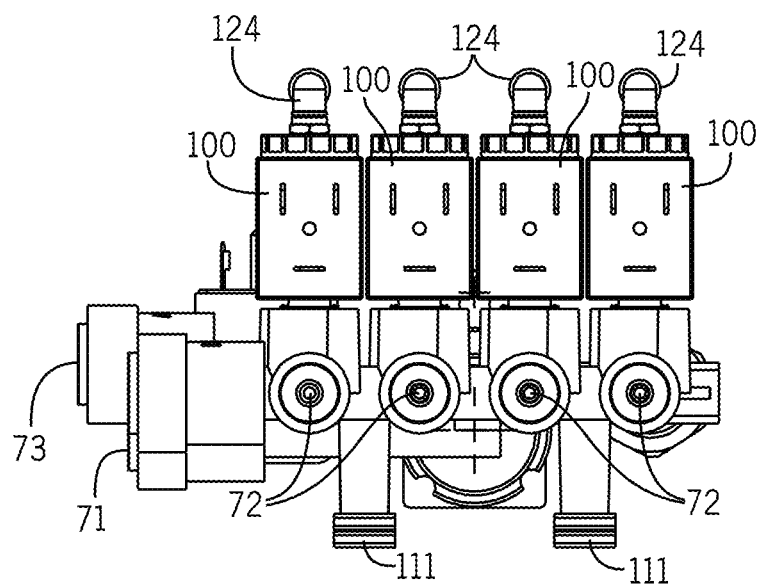
FIG. 13E is a bottom side view of the teat dip manifold of FIG. 13A.

FIG. 12D illustrates the next step, "backflushing," taking place by releasing rinsing fluid into the manifold 50. In this configuration, the rinsing fluid vent 131 is closed and the rinsing fluid valve 130 is opened to permit rinsing fluid to pass through the rinsing fluid check valve 134 and into the galley 86, including the conduits 124. The pressure monitor 114 can be used to check adequacy of the rinsing fluid supply, if desired.

The foregoing detailed description of drawings is provided for clearness of understanding only, and no unnecessary limitations therefrom should be read into the following claims. For example, valve types can be replaced with other valve types, or mixed rather than using a single valve type in the manifold. The valves also need not all be located in the same housing or in any housing because they can be mounted in any desirable way. The manifolds can also be mounted at any suitable location in the dairy or dairy unit to facilitate efficiency and access for maintenance.

The invention claimed is:

1. A method of operating an automated milking stall unit comprising teat dip delivery system, which comprises a teat dip fluid galley in fluid communication with an upstream and downstream valve, the method comprising:
   actuating, by a controller, the upstream and downstream valves from an open position to a closed position;
   filling the galley with fluid after the upstream and downstream valves are actuated to the closed position;

sensing, by a pressure monitor in communication with the galley, a galley pressure while the upstream and downstream valves are in the closed position, wherein the fluid is in the galley during the sensing of the galley pressure; and receiving, by the controller from the pressure monitor, a signal indicating that the sensed galley pressure is outside a predetermined range of galley pressures.

2. The method of claim 1, further comprising:
deactivating, by the controller, at least a portion of the teat dip delivery system responsive to the signal indicating that the sensed galley pressure is outside of the predetermined range of galley pressures.

3. The method of claim 2, wherein, based on the received sensed galley pressure, the controller deactivates the automated milking stall unit.

4. The method of claim 1, wherein the fluid is a rinsing fluid, the method further comprising:

actuating, by the controller, a rinsing fluid vent to a closed position and a rinsing fluid valve to an open position prior to filling the galley with the fluid.

5. The method of claim 1, further comprising:
actuating, by the controller prior to sensing the galley pressure, an air valve and a rinsing fluid valve to a closed position.

6. The method of claim 1, wherein the upstream valve includes a first inlet, a second inlet, and an outlet, wherein the actuation of the upstream valve into the closed position comprises closing the first inlet so that the second inlet and the outlet are fluidly coupled to each other.

7. The method of claim 1, further comprising:
controlling, by the controller, a milking module to divert fluid to a bad milk path responsive to the signal indicating that the sensed galley pressure is outside a predetermined range of galley pressures.

* * * * *